US009511085B2

(12) United States Patent
Kim et al.

(10) Patent No.: US 9,511,085 B2
(45) Date of Patent: Dec. 6, 2016

(54) METHOD FOR CONTROLLING CANCER METASTASIS OR CANCER CELL MIGRATION BY MODULATING THE CELLULAR LEVEL OF LYSYL TRNA SYNTHETASE

(75) Inventors: Sunghoon Kim, Seoul (KR); Jin Woo Choi, Seoul (KR)

(73) Assignee: Medicinal Bioconvergence Research Center, Suwon (KR)

( * ) Notice: Subject to any disclaimer, the term of this patent is extended or adjusted under 35 U.S.C. 154(b) by 897 days.

(21) Appl. No.: 13/059,006

(22) PCT Filed: Aug. 18, 2008

(86) PCT No.: PCT/KR2008/004785

§ 371 (c)(1), (2), (4) Date: Mar. 24, 2011

(87) PCT Pub. No.: WO2010/021415

PCT Pub. Date: Feb. 25, 2010

(65) Prior Publication Data

US 2011/0189195 A1 Aug. 4, 2011

(51) Int. Cl.

| | |
|---|---|
| ***C07K 16/30*** | (2006.01) |
| ***C12N 15/113*** | (2010.01) |
| ***A61K 38/17*** | (2006.01) |
| ***A61K 39/395*** | (2006.01) |
| ***A61K 31/7088*** | (2006.01) |
| ***C12N 9/00*** | (2006.01) |
| ***G01N 33/50*** | (2006.01) |
| *A61K 48/00* | (2006.01) |

(52) U.S. Cl.

CPC ............. *A61K 31/7088* (2013.01); *C12N 9/93* (2013.01); *C12N 15/1137* (2013.01); *C12Y 601/01006* (2013.01); *G01N 33/5017* (2013.01); *A61K 48/00* (2013.01); *C12N 2310/11* (2013.01); *C12N 2310/14* (2013.01)

(58) Field of Classification Search

CPC ............... C07K 16/30; A61K 39/395; A61K 39/39558; A61K 38/17

USPC ................. 424/155.1, 152.1; 530/389.7, 350

See application file for complete search history.

(56) References Cited

U.S. PATENT DOCUMENTS

2008/0219981 A1* 9/2008 Shimada et al. ........... 424/138.1

OTHER PUBLICATIONS

Kim et al. (FASEB J., 2012, 26, 4142-4159).*

Narumi et al. (Jpn. J. Cancer Res. 90, 425-431, Apr. 1999).*

I. Carmi-Levy et al., "Diadenosine tetraphosphate hydrolase is part of the transcriptional regulation network in immunologically activated mast cells", Molecular and Cellular Biology, vol. 28(18), pp. 5777-5784 (Jul. 21, 2008).

S. Gyu Park et al., "Aminoacyl tRNA synthetases and their connections to disease", Proceedings of the National Academy of Sciences, vol. 105(32), pp. 11043-11049 (Aug. 12, 2008).

S. Gyu Park et al., "Do aminoacyl-tRNA synthetases have biological functions other than in protein biosynthesis?", IUBMB Life, vol. 58(9), pp. 556-558, Sep. 2006.

S. Gyu Park et al., "Functional expression of aminoacyl-tRNA synthetases and their interacting factors: new perspectives on housekeepers", Trends in Biochemical Sciences, vol. 30(10), pp. 569-574 (Oct. 2005).

S. Gyu Park et al., "Human lysyl-tRNA synthetase is secreted to trigger proinflammatory response", Proceedings of the National Academy of Sciences, vol. 102(18), pp. 6356-6361 (May 2005).

E. Rayburn et al., "Antisense, RNAi, and gene silencing strategies for therapy: Mission possible or impossible?", Drug Discovery Today, vol. 13(11-12), pp. 513-521 (Jun. 2008).

S. Won Lee et al., "Aminoacyl-tRNA synthetase complexs: beyond translation", Jrl of Cell Science, vol. 177(17), pp. 3725-3734 (Aug. 2004).

* cited by examiner

*Primary Examiner* — Yan Xiao

(74) *Attorney, Agent, or Firm* — Mintz Levin Cohn Ferris Glovsky and Popeo, P.C.; Kongsik Kim; Richard B. Emmons

(57) ABSTRACT

The present invention relates to a novel function of lysyl tRNA synthetase (KRS) which enhances tumor cell migration and affects cancer metastasis via KRS's interaction with laminin receptor (67LR) by its translocation to membrane. More particularly, the present invention relates to a method for modulating cancer metastasis or migration, which comprises regulating intracellular levels of KRS; a composition for preventing or treating cancer; use of expression vector for inhibiting the expression of KRS; a method for preventing or treating cancer; use of an agent for inhibiting an activity of KRS; a method for screening an agent which modulates cancer metastasis or migration; and a method for screening an agent which inhibits the interaction of KRS with 67LR, by said novel function. Thus, KRS can modulate cancer metastasis or migration and furthermore, can modulate intracellular metabolism related to 67LR. The interaction between KRS and 67LR can be used effectively in treating, preventing and/or diagnosing of various diseases or disorders related to the interaction.

4 Claims, 17 Drawing Sheets

SEQUENCE LISTING

```
<160> NUMBER OF SEQ ID NOS: 2

<210> SEQ ID NO 1
<211> LENGTH: 597
<212> TYPE: PRT
<213> ORGANISM: Homo sapiens

<400> SEQUENCE: 1

Met Ala Ala Val Gln Ala Ala Glu Val Lys Val Asp Gly Ser Glu Pro
  1               5                  10                  15

Lys Leu Ser Lys Asn Glu Leu Lys Arg Arg Leu Lys Ala Glu Lys Lys
             20                  25                  30
```

-continued

```
Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140

Tyr Asp Leu Arg Gly Glu Gly Val Lys Leu Gln Val Met Ala Asn Ser
145                 150                 155                 160

Arg Asn Tyr Lys Ser Glu Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro His Leu His Phe Gly Leu Lys Asp Lys Glu
    210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
        275                 280                 285

Glu Leu Asp Met Asn Leu Tyr Met Arg Ile Ala Pro Glu Leu Tyr His
    290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
            340                 345                 350

Ile Thr Glu Lys Met Val Ser Gly Met Val Lys His Ile Thr Gly Ser
        355                 360                 365

Tyr Lys Val Thr Tyr His Pro Asp Gly Pro Glu Gly Gln Ala Tyr Asp
    370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
                405                 410                 415

Glu Glu Thr Arg Lys Ile Leu Asp Asp Ile Cys Val Ala Lys Ala Val
            420                 425                 430

Glu Cys Pro Pro Pro Arg Thr Thr Ala Arg Leu Leu Asp Lys Leu Val
        435                 440                 445
```

```
Gly Glu Phe Leu Glu Val Thr Cys Ile Asn Pro Thr Phe Ile Cys Asp
    450                 455                 460

His Pro Gln Ile Met Ser Pro Leu Ala Lys Trp His Arg Ser Lys Glu
465                 470                 475                 480

Gly Leu Thr Glu Arg Phe Glu Leu Phe Val Met Lys Lys Glu Ile Cys
                485                 490                 495

Asn Ala Tyr Thr Glu Leu Asn Asp Pro Met Arg Gln Arg Gln Leu Phe
            500                 505                 510

Glu Glu Gln Ala Lys Ala Lys Ala Ala Gly Asp Asp Glu Ala Met Phe
        515                 520                 525

Ile Asp Glu Asn Phe Cys Thr Ala Leu Glu Tyr Gly Leu Pro Pro Thr
    530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
                565                 570                 575

Asp Lys Lys Glu Asn Val Ala Thr Thr Asp Thr Leu Glu Ser Thr Thr
            580                 585                 590

Val Gly Thr Ser Val
        595
```

<210> SEQ ID NO 2
<211> LENGTH: 1794
<212> TYPE: DNA
<213> ORGANISM: Homo sapiens

<400> SEQUENCE: 2

```
atggcggccg tgcaggcggc cgaggtgaaa gtggatggca gcgagccgaa actgagcaag     60

aatgagctga agagacgcct gaaagctgag aagaaagtag cagagaagga ggccaaacag    120

aaagagctca gtgagaaaca gctaagccaa gccactgctg ctgccaccaa ccacaccact    180

gataatggtg tgggtcctga ggaagagagc gtggacccaa atcaatacta caaaatccgc    240

agtcaagcaa ttcatcagct gaaggtcaat ggggaagacc catacccaca caagttccat    300

gtagacatct cactcactga cttcatccaa aaatatagtc acctgcagcc tggggatcac    360

ctgactgaca tcaccttaaa ggtggcaggt aggatccatg ccaaaagagc ttctggggga    420

aagctcatct tctatgatct tcgaggagag gggggtgaagt tgcaagtcat ggccaattcc    480

agaaattata aatcagaaga agaatttatt catattaata acaaactgcg tcggggagac    540

ataattggag ttcaggggaa tcctggtaaa accaagaagg gtgagctgag catcattccg    600

tatgagatca cactgctgtc tccctgtttg catatgttac ctcatcttca ctttgggctc    660

aaagacaagg aaacaaggta tcgccagaga tacttggact tgatcctgaa tgactttgtg    720

aggcagaaat ttatcatccg ctctaagatc atcacatata taagaagttt cttagatgag    780

ctgggattcc tagagattga aactcccatg atgaacatca tcccaggggg agccgtggcc    840

aagcctttca tcacttatca caacgagctg gacatgaact tatatatgag aattgctcca    900

gaactctatc ataagatgct tgtggttggt ggcatcgacc gggtttatga aattggacgc    960

cagttccgga atgaggggat tgatttgacg cacaatcctg agttcaccac ctgtgagttc   1020

tacatggcct atgcagacta tcacgatctc atggaaatca cggagaagat ggtttcaggg   1080

atggtgaagc atattacagg cagttacaag gtcacctacc acccagatgg cccagagggc   1140

caagcctacg atgttgactt caccccaccc ttccggcgaa tcaacatggt agaagagctt   1200

gagaaagccc tggggatgaa gctgccagaa acgaacctct ttgaaactga agaaactcgc   1260
```

-continued

```
aaaattcttg atgatatctg tgtggcaaaa gctgttgaat gccctccacc tcggaccaca   1320

gccaggctcc ttgacaagct tgttggggag ttcctggaag tgacttgcat caatcctaca   1380

ttcatctgtg atcacccaca gataatgagc cctttggcta aatggcaccg ctctaaagag   1440

ggtctgactg agcgctttga gctgtttgtc atgaagaaag agatatgcaa tgcgtatact   1500

gagctgaatg atcccatgcg gcagcggcag ctttttgaag aacaggccaa ggccaaggct   1560

gcaggtgatg atgaggccat gttcatagat gaaaacttct gtactgccct ggaatatggg   1620

ctgcccccca cagctggctg ggcatgggc attgatcgag tcgccatgtt tctcacggac    1680

tccaacaaca tcaaggaagt acttctgttt cctgccatga aacccgaaga caagaaggag   1740

aatgtagcaa ccactgatac actggaaagc acaacagttg gcacttctgt ctag         1794
```

METHOD FOR CONTROLLING CANCER METASTASIS OR CANCER CELL MIGRATION BY MODULATING THE CELLULAR LEVEL OF LYSYL TRNA SYNTHETASE

CROSS-REFERENCES TO RELATED APPLICATIONS

This application is a U.S. national phase application, pursuant to 35 U.S.C. §371, of PCT/KR2008/004785, filed Aug. 18, 2008, designating the United States. The entire contents of the aforementioned patent application is incorporated herein by this reference.

TECHNICAL FIELD

The present invention relates to a novel function of lysyl tRNA synthease. More specifically, it relates to a method for controlling cancer metastasis or cancer cell migration by modulating an cellular level of lysyl tRNA synthetase, an use of an expression vector comprising a construct inhibiting KRS expression for preventing or treating cancer, an use of an agent inhibiting KRS activity for preventing or treating cancer, a method for screening an agent which modulates cancer metastasis or cancer cell migration, a method for screening an agent inhibiting an interaction between KRS and 67LR.

BACKGROUND ART

A tumor is developed by uncontrollable disordered abnormal cell proliferation. Especially, if this tumor shows a destructive growth, invasiveness and metastasis, it is regarded as a malignant cancer. Invasiveness is a character to infiltrate or destroy surrounding tissues, and in particular, a basal layer forming a boundary of tissues is destroyed by the character, resulting in the local spread and sometimes inflow of a tumor through circulatory system. Metastasis means the spread of tumor cells from the original birthplace to other areas through lymphatic or blood vessels. In a broad sense, metastasis also means the direct extension of tumor cells through serous body cavity or other space.

These days, surgical operation, radiotherapy and chemotherapy are widely used for the treatment of cancer singly or jointly. The surgical operation is a way to remove diseased tissues. Thus, tumors in specific regions such as breast, colon and skin can be effectively removed by the surgical operation. However, a tumor in vertebra or dispersive tumor like leukemia cannot be properly treated by the surgical operation.

Chemotherapy blocks cell replication or metabolism, and has been used for the treatment of breast cancer, lung cancer and testicular cancer. Though, patients with cancers who have been treated by chemotherapy have seriously suffered from the side effects of systemic chemotherapy. Motion sickness and vomiting are common but serious examples of all. The side effects of chemotherapy can even affect the life of a patient since they might drop the adaptability of a patient rapidly. Besides, DLT (Dose Limiting Toxicity) is also one of major side effects of chemotherapy, which draws a careful attention in the administration of a medicine. Mucositis is an example of DLT against anticancer agents such as 5-fluorouracil which is an antimetabolic cytotoxic agent, and methotrexate, and anticancer antibiotics like doxorubicin. If a patient suffers seriously from such side effects of chemotherapy, he or she should be hospitalized and given an anodyne for reducing pain. So, side effects of chemotherapy and radiotherapy are the biggest problem for the treatment of cancer patients.

Gene therapy is a method to treat or prevent diseases caused by the genetic variation in human cells, for example various genetic disorders, cancers, cardiovascular diseases, infective diseases, and auto-immune diseases, by taking advantage of DNA recombination technique, that is, a therapeutic gene is inserted into a patient to correct genetic defect or to promote or add functions of cells. More precisely, gene therapy is to treat a disease by sending a therapeutic gene to a target organ in order to induce the expression of therapeutic or normal protein in damaged cells. Gene therapy has advantages such as excellent specificity and improvement of recovery rate and speed, which are difficult to be regulated by other medicine, which enables long-term administration. Gene therapy is not for treating symptoms of a disease but for curing or eliminating the cause of the disease. For the success of the therapy, it is important to deliver a therapeutic gene to a target cell to improve its expression rate, which is essential technique in gene therapy.

A gene carrier is a necessary mediator for the insertion of a therapeutic gene to a target cell. An ideal gene carrier has to be no harmful for human, mass-produced, has to carry a gene to a target cell efficiently and has to express the gene continuously. Preparation of a Gene Carrier is a Core Technique in Gene therapy. Most representative gene carriers widely used for gene therapy today are viral carriers such as adenovirus, adeno-associated virus, retrovirus and non-viral carriers such as liposome, polyethyleneamine, etc.

As gene therapy strategies for controlling tumor cells, methods of using a tumor suppressor gene, using a replication-competent oncolytic virus, using a suicide gene and using an immunoregulatory gene, etc, have been used. The method of using a tumor suppressor gene is to treat cancer by delivering a tumor suppressor gene such as p53 into a patient specifically, where the gene is defected or deformed. In addition, the method of using a replication-competent oncolytic virus is to treat cancer by exploiting the damaged activity of tumor suppressor gene in tumor tissues by transferring a viral gene carrier that is able to be growing specifically in tumor cells to a human body. These two methods are the strategies to kill tumor cells directly. Alternately, the method of using a suicide gene is included in this category. A representative example of a suicide gene therapy is to treat disease by delivering a HSV-TK gene and chemical anticancer agents such as ganciclovir, which can induce death of tumor cells. On the contrary, the method to introduce an immunoregulatory gene is a kind of indirect treatment strategies, which carries one or more of the genes such as interleukin 12, interleukin 4, interleukin 7, gamma-interferon and tumor necrosis factor, etc, into a living body in order to provoke T cells to recognize tumor cells or induce apoptosis by blocking a tumor developing protein. On the other hand, the method to kill tumor cells by blocking nutrient supply by expressing angiogenesis inhibiting factors such as angiostatin or endostatin, etc, is also included in the category of indirect treatment strategies.

Metastatic spread is a critical determinant for the lethality of cancer. 67 kDa laminin receptor (67LR) is non-integrin type receptor embedded in plasma membrane and associated with cancer invasion and metastasis (Nelson, J. et al. The 67 kDa laminin receptor: structure, function and role in disease. Biosci. Rep. 28, 33-48 (2008)). 67LR is generated from dimerization of its 37 kDa precursor (37LRP) although molecular detail of this conversion process is not understood. 37LRP is identical to ribosomal subunit p40 that is involved in the formation of polysome (Auth, D. & Brawerman, G. A 33-kDa polypeptide with homology to the laminin receptor: component of translation machinery. Proc. Natl. Acad. Sci. USA 89, 4368-4372 (1992)). 67LR is often observed at high level in a variety of cancers (Nelson, J. et al. The 67 kDa laminin receptor: structure, function and role in disease. Biosci. Rep. 28, 33-48 (2008); Menard, S., Castronovo, V., Tagliabue, E. & Sobel, M. E. New insights into the metastasis-associated 67 kD laminin receptor. J. Cell. Biochem. 67, 155-165 (1997)). However, the regulator and molecular mechanism for the membrane residency of 67LR have not been determined yet. In this work, the present inventors found that lysyl-tRNA synthetase (KRS) enhances cell migration and cancer metastasis by stabilizing 67LR at plasma membrane.

KRS belongs to aminoacyl-tRNA synthetases (ARSs) that ligate their cognate amino acids and tRNAs for protein synthesis. These ancient enzymes show pleiotropic functions in addition to their catalytic activities (Park, S. G., Ewalt, K. L. & Kim, S. Functional expansion of aminoacyl-tRNA synthetases and their interacting factors: new perspectives on housekeepers. Trends Biochem. Sci. 30, 569-574 (2005)). Besides, several mammalian ARSs including KRS form a macromolecular complex (Lee, S. W., Cho, B. H., Park, S. G. & Kim, S. Aminoacyl-tRNA synthetase complexes: beyond translation. *J. Cell. Sci.* 117, 3725-3734 (2004); Han, J. M., Kim, J. Y. & Kim, S. Molecular network and functional implications of macromolecular tRNA synthetase complex. *Biochem. Biophys. Res. Commun.* 303, 985-993 (2003)), which serve as molecular reservoir (Ray, P. S., Arif, A. & Fox, P. Macromolecular complexes as depots for releasable regulatory proteins. *Trends Biochem. Sci.* 32, 158-164 (2007).), to control multiple functions of the component proteins. Human KRS contains unique N-terminal extension involved in the interactions with RNA and other proteins (Rho, S. B. et al. Genetic dissection of protein-protein interactions in multi-tRNA synthetase complex. *Proc. Natl. Sci. Acad. USA* 96, 4488-4493 (1999); Francin, M., Kaminska, M., Kerjan, P. & Mirande. M. The N-terminal domain of mammalian Lysyl-tRNA synthetase is a functional tRNA-binding domain. *J. Biol. Chem.* 277, 1762-1769 (2002)).

DISCLOSURE

Technical Problem

To determine the significance of this peptide in relation to the functional versatility of human KRS, the present inventors isolated the N-terminal 116 aa peptide of human KRS and used it as the bait for the screening of its binding proteins from HeLa cell cDNA library using yeast two-hybrid system. From the screening, the present inventors identified 37LRP/p40 as one of the potential binding proteins and investigated the functional implication for the interaction between KRS and laminin receptor in this work. To determine the significance of this peptide in relation to the functional versatility of human KRS, the present inventors isolated the N-terminal 116 amino acids peptide of human KRS and used it as the bait for the screening of its binding proteins from HeLa cell cDNA library using yeast two-hybrid system. From the screening, the present inventors identified 37LRP/p40 as one of the potential binding proteins and investigated the functional implication for the interaction between KRS and laminin receptor in this work.

As a result, the present inventors disclosed that lysyl-t-RNA-synthetase (KRS) enhances cell migration and tumor metastasis by stabilizing 67LR in a plasma membrane to have an effect on cancer metastasis or cancer cell migration through a laminin receptor in the plasma membrane, thereby completing the present invention.

An object of the present invention is to provide a novel use of lysyl-t-RNA-synthetase regarding cancer metastasis or cancer cell migration.

To achieve the above object, the present invention provides a method for controlling cancer metastasis by modulating a cellular level of lysyl tRNA synthetase.

To achieve another object, the present invention provides a method for controlling cancer cell migration by modulating a cellular level of lysyl tRNA synthetase.

To achieve still another object, the present invention provides a composition for preventing and treating cancer comprising an expression vector comprising a promoter and a polynucleotide operably linked thereto, or an antibody against KRS as an effective ingredient, wherein the polynucleotide is encoding antisense RNA or siRNA against the KRS polynucleotide.

To achieve still another object, the present invention provides a method for preventing and treating cancer comprising administering to a subject in need thereof an effective amount of an expression vector comprising a promoter and a polynucleotide operably linked thereto, or an antibody against KRS, wherein the polynucleotide is encoding antisense RNA or siRNA against the KRS polynucleotide.

To achieve still another object, the present invention provides a use of an expression vector comprising a promoter and a polynucleotide operably linked thereto, or an antibody against KRS for preparation an anti-cancer agent, wherein the polynucleotide is encoding antisense RNA or siRNA against the KRS polynucleotide.

To achieve still another object, the present invention provides a composition for preventing and treating cancer comprising an agent inhibiting KRS activity as an active ingredient.

To achieve still another object, the present invention provides a method for preventing and treating cancer comprising administering to a subject in need thereof an effective amount of an agent inhibiting KRS activity.

To achieve still another object, the present invention provides an use of an agent inhibiting KRS activity for preparation a cancer therapeutic agent.

In another aspect, the present invention provides a method for screening an agent which modulates cancer metastasis or cancer cell migration comprising:

(a) contacting a testing agent with KRS in the presence of the testing agent;

(b) measuring activity of KRS and selecting testing agent which changes activity of KRS; and (c) testing whether the selected agent regulates tumor metastasis or cancer cell migration.

In another aspect, the present invention provides a method for screening an agent inhibiting an interaction between KRS and 67LR comprising:

(a) contacting a testing agent with KRS and laminin receptor (67LR) in the presence of the testing agent; and (b) testing whether the selected agent regulates an interaction between KRS and laminin receptor.

In another aspect, the present invention provides a method for diagnosis of lung cancer or breast cancer comprising:

(a) analyzing overexpression of 67LR in a sample; and (b) analyzing overexpression of KRS in the 67LR overexpressed sample.

Technical Solution

Hereinafter, the present invention will be described in detail.

In the present invention, the present inventors first identified that KRS has an effect on cancer metastasis or cancer cell migration. That is, the present inventor identified that KRS has an effect on cancer metastasis or cancer cell migration through a laminin receptor in the plasma membrane.

DEFINITION

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOTY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY. In addition, the following definitions are provided to assist the reader in the practice of the invention.

An "expression", as used herein, refers formation of protein or nucleic acid in cells.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The term "isolated" means that the material is removed from its original environment (e.g., the natural environment if it is naturally occurring). For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

The term "modulate" with respect to KRS bioactivities refers to a change in the cellular level of KRS. Modulation of KRS bioactivities can be up-regulation (i.e., activation or stimulation) or down-regulation (i.e. inhibition or suppression). For example, modulation may cause a change in cellular level of KRS, stability of protein, enzymatic modification (e.g., phosphorylation) of KRS, binding characteristics (e.g., binding to a target transcription regulatory element), or any other biological, functional, or immunological properties of KRS. The change in activity can arise from, for example, an increase or decrease in expression of the KRS gene, the stability of mRNA that encodes the KRS protein, translation efficiency, or from a change in other bioactivities of the KRS transcription factor (e.g., regulating expression of a KRS-responsive gene). The mode of action of a KRS modulator can be direct, e.g., through binding to the KRS protein or to genes encoding the KRS protein. The change can also be indirect, e.g., through binding to and/or modifying (e.g., enzymatically) another molecule which otherwise modulates KRS (e.g., a kinase that specifically phosphorylates KRS).

The term "polypeptide" is used interchangeably herein with the terms "polypeptides" and "protein(s)", and refers to a polymer of amino acid residues, e.g., as typically found in proteins in nature.

The term "KRS polypeptide," refers to a polypeptide known as lysyl tRNA synthetase. The said KRS polypeptide may be a polypeptide having an amino acid sequence of SEQ ID NO: 1 (GenBank Accession No: NP_005539.1). And the inventive KRS includes functional equivalents thereof.

The term "functional equivalents" refers polypeptide comprising the amino acid sequence having at least 70% amino acid sequence homology (i.e., identity), preferably at least 80%, and more preferably at least 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% amino acid sequence homology, that exhibit substantially identical physiological activity to the polypeptide of SEQ ID NO: 1. The "substantially identical physiological activity" means interaction with laminin receptor of plasma membrane and regulation of tumor metastasis or tumor cell migration. The functional equivalents may include, for example peptides produced by as a result of addition, substitution or deletion of some amino acid of SEQ ID NO:1. Substitutions of the amino acids are preferably conservative substitutions. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (H is, Lys, Arg, Gln, Asn) and sulfur-containing amino acids (Cys, Met). Furthermore, the functional equivalents also include variants with deletion of some of the amino acid sequence of the inventive KRS. Deletion or substitutions of the amino acids are preferably located at regions that are not directly involved in the physiological activity of the inventive polypeptide. And deletion of the amino acids is preferably located at regions that are not directly involved in the physiological activity of the KRS. In addition, the functional equivalents also include variants with addition of several amino acids in both terminal ends of the amino acid sequence of the KRS or in the sequence. Moreover, the inventive functional equivalents also include polypeptide derivatives which have modification of some of the chemical structure of the inventive polypeptide while maintaining the fundamental backbone and physiological activity of the inventive polypeptide. Examples of this modification include structural modifications for changing the stability, storage, volatility or solubility of the inventive polypeptide.

Sequence identity or homology is defined herein as the percentage of amino acid residues in the candidate sequence that are identical with amino acid sequence of KRS (SEQ ID NO: 1), after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the amino acid sequence of KRS shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix; see Dayhoff et al., in Atlas of Protein Sequence and Structure, vol. 5, supp. 3 (1978)) can be used in conjunction with the computer program. For example, the percent identity can be calculated as the follow.

The total number of identical matches multiplied by 100 and then divided by the sum of the length of the longer sequence within the matched span and the number of gaps introduced into the longer sequences in order to align the two sequences.

The polypeptide according to the present invention can be prepared by separating from nature materials or genetic engineering methods. For example, a DNA molecule encoding the KRS or its functional equivalents (ex: SEQ ID NO: 2 (Genbank Accession No. D32053)) is constructed according to any conventional method. The DNA molecule may synthesize by performing PCR using suitable primers. Alternatively, the DNA molecule may also be synthesized by a standard method known in the art, for example using an automatic DNA synthesizer (commercially available from Biosearch or Applied Biosystems). The constructed DNA molecule is inserted into a vector comprising at least one expression control sequence (ex: promoter, enhancer) that is operatively linked to the DNA sequence so as to control the expression of the DNA molecule, and host cells are transformed with the resulting recombinant expression vector. The transformed cells are cultured in a medium and condition suitable to express the DNA sequence, and a substantially pure polypeptide encoded by the DNA sequence is collected from the culture medium. The collection of the pure polypeptide may be performed using a method known in the art, for example, chromatography. In this regard, the term "substantially pure polypeptide" means the inventive polypeptide that does not substantially contain any other proteins derived from host cells. For the genetic engineering method for synthesizing the inventive polypeptide, the reader may refer to the following literatures: Maniatis et al., *Molecular Cloning: A Laboratory Manual, Cold Spring Harbor Laboratory* 1982; Sambrook et al., *Molecular Cloning; A Laboratory Manual*, Cold Spring Harbor Press, N.Y., Second (1998) and Third (2000) Editions; *Gene Expression Technology, Method in Enzymology, Genetics and Molecular Biology, Method in Enzymology, Guthrie & Fink* (eds.), Academic Press, San Diego, Calif. 1991; and Hitzeman et al., J. Biol. Chem., 255, 12073-12080 1990.

Alternatively, the inventive polypeptide can be chemically synthesized easily according to any technique known in the art (Creighton, Proteins: Structures and Molecular Principles, W.H. Freeman and Co., NY, 1983). As a typical technique, they are not limited to, but include liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

The inventive laminin receptor (67LR) of 67 kDa is plasma membrane-embeded, non-integrin receptor and for example, it may have a nucleotide sequence or amino acid sequence any one disclosed in Genbank Accession No. NM_002295, 537431, AF284768, 537431, AF284768, J03799, XP 370865, XP 001083023.

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides.

The term "the nucleotide encoding KRS or functional equivalents thereof" may have a nucleic acid encoding a polypeptide having the amino acid sequence of SEQ ID NO: or a polypeptide having the amino acid sequence homology of at least 70% to the polypeptide. The nucleic acid includes DNA, cDNA or RNA. The polynucleotide may have a nucleotide sequence encoding the amino acid sequence of SEQ ID NO: 1 or an amino acid sequence homology of at least 70% to SEQ ID NO: 1. Preferably, the polynucleotide comprises the nucleotide sequence of SEQ ID NO. 2. The nucleic acid can be isolated from a natural source or be prepared by a genetic engineering method known in the art.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence.

As used herein, the term "effective amount" refers to an amount showing an effect of the modulating KRS bioactiviy (ex: cellular levels etc.) differently to normal cells or tissues or the inhibiting the ubiquitination of KRS.

As used herein, "contacting" has its normal meaning and refers to combining two or more agents (e.g., two polypeptides) or combining agents and cells (e.g., a protein and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably. More specifically, test agents that can be identified with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules. Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field.

Known pharmacological agents can be subject to directed or random chemical modifications, such as acylation, alkylation, esterification, amidification to produce structural analogs.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides.

The test agents can also be "nucleic acids". Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. A number of assays are available for such screening, e.g., as described in Schultz (1998) Bioorg Med Chem Lett 8:2409-2414; The present inventorsller (1997) Mol Divers. 3:61-70; Fernandes (1998) Curr Opin Chem Biol 2:597-603; and Sittampalam (1997) Curr Opin Chem Biol 1:384-91.

Libraries of test agents to be screened with methods of the present invention can also be generated based on structural studies of the KRS, its fragment or its analog. Such structural studies allow the identification of test agents that are more likely to bind to the KRS. The three-dimensional structures of the KRS can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D.C. Crothers (Benjamin Cummings, Menlo Park 1979). Computer modeling of structures of KRS provides another means for designing test agents for screening KRS. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interrscience, New York 1986).

Hereinafter, the present invention will be described in detail.

The present inventors disclosed that the inventive KRS interacts with 67LR through translocation of KRS into plasma membrane, and so enhances tumor (or cancer) cell migration, thereby having an effect on cancer metastasis. In addition, we also disclosed that KRS overexpression or inhibition of KRS expression can modulate tumor (or cancer) cell metastasis through in vivo experiments using mice.

Accordingly, the present invention provides a method for controlling cancer metastasis by modulating a cellular level of lysyl tRNA synthetase.

To be explained more in detail, if the cellular level of the inventive lysyl tRNA synthetase is reduced, the cancer metastasis may be suppressed, and if the cellular level of the inventive lysyl tRNA synthetase is increased, the cancer metastasis may be stimulated.

The reduction or increase of the cellular level is regulated with various well known methods in the art as described above. For example, but not limited thereto, the cellular level may be controlled through transcriptional regulation or post-transcriptional regulation. The transcriptional regulation may be performed by the method of enhancing a gene expression known in the art, e.g., the method of enhancing a gene expression by preparing a recombinant expression vector comprising a polynucleotide encoding KRS or functional equivalent thereof operably linked to a promoter, or the method for inserting an expression regulating sequence to enhance an expression of a gene encoding KRS or functional equivalent thereof around the gene, or the method for inhibiting gene expression, e.g., the method inhibiting promoter activity or protein function by inducing mutation in promoter or gene region, the method for expressing antisense gene, or siRNA or microRNA.

The post-transcriptional regulation may be performed by the method for enhancing or suppressing protein expression known in the art, e.g., the method for enhancing or suppressing stability of mRNA of the gene encoding KRS or functional equivalent thereof, the method for enhancing or suppressing stability of the protein or the polypeptide, or the method for enhancing or suppressing activity of the protein or the polypeptide.

For concrete example of the above mentioned methods, it can induce cosuppression via transformation using DNA sequence encoding RNA acting to mRNA such as type 1 intron, M1 RNA type, hammerhead type or hairpin type or micro RNA type, or transformation using DNA having the same or similar sequence to a target gene.

Preferably, in the present invention, the method for controlling of the cellular level of KRS or a functional equivalent thereof may be performed by the method for enhancing or suppressing expression of a polynucleotide encoding the polypeptide. The method for enhancing or suppressing may be used by skilled persons in the art, for example, through preparing of a recombinant expression vector comprising a polynucleotide encoding KRS or a functional equivalent thereof operably linked to a promoter to enhance the expression of the polynucleotide, or through preparing of a recombinant expression vector comprising antisense RNA polynucleotide or siRNA polynucleotide against the polynucleotide encoding KRS or a functional equivalent thereof operably linked to a promoter to suppress the expression of the polynucleotide. The polynucleotide encoding KRS or a functional equivalent thereof may have the nucleotide sequence represented by SEQ ID. NO. 2, preferably.

In addition, the present invention provides a method for controlling cancer cell migration by modulating a cellular level of lysyl tRNA synthetase, and the modulation the cellular level is as same as described above.

In addition, when the expression of the inventive KRS is suppressed, tumor (or cancer) metastasis is inhibited, the present invention provides a composition for preventing and treating cancer comprising an expression vector comprising a promoter and a structural gene suppressing expression of KRS operably linked thereto, or an antibody against KRS as an effective ingredient. The structural gene suppressing expression of KRS may be antisense RNA or siRNA against a polynucleotide encoding KRS.

The diseases which can be applied the inventive composition may be cancers. The cancers include, but are not limited to, colon cancer, lung cancer, liver cancer, stomach cancer, esophagus cancer, pancreatic cancer, gall bladder cancer, kidney cancer, bladder cancer, prostate cancer, testis cancer, cervical cancer, endometrial carcinoma, choriocarcinoma, ovarian cancer, breast cancer, thyroid cancer, brain tumor, head or neck cancer, malignant melanoma, lymphoma, aplastic anemia.

The "promoter" means a DNA sequence regulating the expression of nucleic acid sequence operably linked to the promoter in a specific host cell, and the term "operably linked" means that one nucleic acid fragment is linked to other nucleic acid fragment so that the function or expression thereof is affected by the other nucleic acid fragment. Additionally, the promoter may include an operator sequence for controlling transcription, a sequence encoding a suitable mRNA ribosome-binding site, and sequences controlling the termination transcription and translation. Additionally, it may be constitutive promoter which constitutively induces the expression of a target gene, or inducible promoter which induces the expression of a target gene at a specific site and a specific time, and examples thereof include a SV40 promoter, CMV promoter, CAG promoter (Hitoshi Niwa et al., Gene, 108:193-199, 1991; Monahan et al., *Gene Therapy,* 7:24-30, 2000), CaMV 35S promoter (Odell et al., Nature 313:810-812, 1985), Rsyn7 promoter (U.S. patent application Ser. No. 08/991,601), rice actin promoter (McElroy et al., *Plant Cell* 2:163-171, 1990), Ubiquitin promoter (Christensen et al., *Plant Mol. Biol.* 12:619-632, 1989), ALS promoter (U.S. patent application Ser. No. 08/409,297). Also usable promoters are disclosed in U.S. Pat. Nos. 5,608,149; 5,608,144; 5,604,121; 5,569,597; 5,466,785; 5,399,680; 5,268,463; and 5,608,142, etc.)

Meanwhile, the present invention provides a method for preventing and treating cancer comprising administering to a subject in need thereof an effective amount of an expression vector comprising a promoter and a structural gene suppressing expression of KRS operably linked thereto, or an antibody against KRS. As the structure gene is described above, the present invention provides a method for preventing and treating cancer comprising administering to a subject in need thereof an effective amount of an expression vector comprising a promoter and a polynucleotide operably linked thereto, or an antibody against KRS as an effective ingredient, wherein the polynucleotide is encoding antisense RNA or siRNA against the KRS polynucleotide.

As used herein, the "effective amount" refers to the amount of inventive expression vector effective in treating tumor, and the "subject" refers to animals, preferably, animals comprising human and it may be cells, tissues, organs originated from the animals. The subject may be patient in need of treatment.

In addition, the present invention provides an use of an expression vector comprising a promoter and a structural gene suppressing expression of KRS operably linked thereto, or an antibody against KRS for preparation an anti-cancer agent. More specifically, the present invention provides an use of an expression vector comprising a promoter and a polynucleotide operably linked thereto, or an antibody against KRS for preparation an anti-cancer agent, wherein the polynucleotide is encoding antisense RNA or siRNA against the KRS polynucleotide. Regarding the above promoter, KRS, expression vector, applied cancers are as can be seen from the foregoing.

The term antibody against KRS as used herein means a specific protein molecule that indicates an antigenic region concerning antigenic region of KRS. With respect to the objects of the present invention, the antibody refers to an antibody specifically binding KRS and includes all polyclonal, monoclonal and recombinant antibodies.

The antibodies against the KRS may be easily prepared in accordance with conventional technologies known to one skilled in the art. Polyclonal antibodies may be prepared by a method widely known in the art, which includes injecting the KRS protein into an animal and collecting blood samples from the animal to obtain serum containing antibodies. Such polyclonal antibodies may be prepared from a certain animal host, such as goats, rabbits, sheep, monkeys, horses, pigs, cows and dogs.

Monoclonal antibodies may be prepared by a method widely known in the art, such as a hybridoma method (Kohler and Milstein, *European Journal of Immunology,* 6:511-519 (1976)) or a phage antibody library technique (Clackson et al, *Nature,* 352:624-628 (1991); and Marks et al, *J. Mol. Biol.,* 222:58, 1-597 (1991)).

The hybridoma method employs cells from an immunologically suitable host animal injected with a diagnostic marker protein of lung cancer as an antigen, such as mice, and a cancer or myeloma cell line as another group. Cells of the two groups are fused with each other by a method widely known in the art, for example, using polyethylene glycol, and antibody-producing cells are proliferated by a standard tissue culture method. After uniform cell colonies are obtained by subcloning using a limited dilution technique, hybridomas capable of producing an antibody specific for the diagnostic marker protein of lung cancer are cultivated in large scale in vitro or in vivo according to a standard technique. Monoclonal antibodies produced by the hybridomas may be used in an unpurified form, but are preferably used after being highly purified by a method widely known in the art so as to obtain best results. The phage antibody library method includes constructing a phage antibody library in vitro by obtaining genes for antibodies (single-chain fragment variable (scFv)) to a variety of intracellular lung cancer markers and expressing them in a fusion protein form on the surface of phages, and isolating monoclonal antibodies binding to lung cancer-specific proteins from the library. Antibodies prepared by the above methods are isolated using gel electrophoresis, dialysis, salting out, ion exchange chromatography, affinity chromatography, and the like. In addition, the antibodies of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2 and Fv.

In addition, so the present inventor disclosed that in case of decreasing the cellular level of KRS, it suppress cancer metastasis, thereby preventing and treating cancer, and the present invention provides a composition for preventing and treating cancer comprising a KRS activity inhibitor as an effective ingredient. In addition, the present invention provides a method for preventing and treating cancer comprising administering to a subject in need thereof effective amount of a KRS activity inhibitor and a use of a KRS activity inhibitor for preparing anti-cancer agent. The type of cancer, the subject, effective amount and so on are the same as described above.

The KRS activity inhibitor means the agent for suppressing expression of KRS, that is, suppressing expression in the level of mRNA or protein, for example, it may be antisense RNA or siRNA against KRS, or competitive inhibitor or non-competitive inhibitor for suppressing activity of expressed KRS, for example, antibodies against KRS, but not limited thereto.

In case of decreasing the cellular level of KRS, since it inhibits cancer metastasis to prevent and treat cancer, the inventive composition, method and use may be applied as themselves as well as may be applied as combinations with well known method for preventing and treating cancer in the art. That is, since the inventive composition, method and etc. can suppress cancer metastasis, if it is applied together with well known anticancer drugs or methods for preventing and treating cancer, it suppresses cancer metastasis and would be effective for full recovery through treatment of main tumor region.

The antitumor agent or the method for preventing and treating that can be used in combination with the polypeptide of the present invention may be any one that is used for treatment of a tumor. For example, paclitaxel, doxorubicin, vincristine, daunorubicin, vinblastine, daunorubicin D, docetaxel, etoposide, teniposide, bisantrene, homoharringtonine, Gleevec (STI-571), cisplatin, 5-fluorouracil, Adriamycin, methotrexate, busulfan, chlorambucil, cyclophosphamide, melphalan, nitrogen mustard, nitrosourea, etc. may be included. The amount of the peptide of the present invention included in the composition of the present invention may be different depending on the kind and amount of the anticancer drug that the peptide binds to.

The combinations between the agents, and the composition or the method of the present invention may be performed depending on the kind and the amount of the anticancer drug appropriately by the skilled person in the art.

The inventive expression vector, the agent inhibiting activities of antibody against KRS or KRS may be administered orally or parenterally. The oral administration may comprise hypoglossal method. Parenteral administration methods are not limited, but include injection methods such as hypodermical, intramuscular and intravenous, and dropping method. The inventive expression vector, the agent inhibiting activities of antibody against KRS or KRS may be prepared into various types of pharmaceutical compositions by mixing with pharmaceutically acceptable carriers. As used herein, the term "pharmaceutically acceptable" means what is physiologically acceptable and, when administered to human beings, generally does not cause allergic reactions, such as gastrointestinal disorder and dizziness, or similar reactions thereto. In the case of an oral formulation, a binding agent, a lublitant, a solutionizer, an exipient, a solubilizer, a dispersing agent, a stabilizer, a suspending agent, a colorant and a flavor may be used. In the case of an injection formulation, a buffer, a preservative, a painless agent, a solubilizer, a isotonic agent and a stabilizer may be used and In the case of an or parenteral formulation, a base, an exipient, a lubricant and a preservative may be used. The pharmaceutical composition comprising the inventive expression vector, the agent inhibiting activities of antibody against KRS or KRS may be prepared into various types by mixing with pharmaceutically acceptable carriers. For example, in the case of an oral formulation, it may be formulated into tablet, troche, capsule, elixir, suspension, syrup, and wafer and in the case of injection formulation; it may be prepared into a single dose ampoule or a multiple dose ampoule.

The total effective amount of the inventive expression vector, the agent inhibiting activities of antibody against KRS or KRS can be administered to a subject as a single dose, or can be administered using a fractionated treatment protocol, in which the multiple doses are administered over a more prolonged period of time. The composition comprising the inventive expression vector, the agent inhibiting activities of antibody against KRS or KRS can be varied in amount of effective component depending on the severity and/or object of disease, but normally, it may be administered by 0.1 μg to 100 mg, and preferably 1 μg to 10 mg and multiple times a day. However, one skilled in the art would know that the concentration of the inventive expression vector or the agent inhibiting activities of KRS required to obtain an effective dose in a subject depends on many factors including the age, body weight, health condition, disease severity, diet and excretion of the subject, the route of administration, the number of treatments to be administered, and so forth. In view of these factors, any person skilled in the art can determine the suitable effective dose of the inventive expression vector or the agent inhibiting activities of KRS. No particular limitation is imposed on the formulation, administration route and administration mode of the pharmaceutical composition according to the present invention, as long as the composition shows the effects of the present invention.

The inventive compositions may be administered to patients with the amount which is effective for preventing disease. Generally, the effective amount of the inventive composition is about 0.0001 to 100 mg/kg body weight/day. Preferably 0.01 to 1 mg/kg body the present weight/day. It may be suitably determined by considering various factors, such as age, body weight, health condition, sex, disease severity, diet and excretion of a subject in need of treatment, as well as administration time and administration route.

Meanwhile, the said expression vector can be introduced into a target cell by any method known in the art, such as infection, transfection or transduction.

A gene transfer method using a plasmid expression vector is a method of transferring a plasmid DNA directly to mammalian cells, which is an FDA-approved method applicable to human beings (Nabel, E. G., et al., *Science,* 249: 1285-1288, 1990). Unlike viral vectors, the plasmid DNA has an advantage of being homogeneously purified. Plasmid expression vectors which can be used in the present invention include mammalian expression plasmids known in the pertinent art. For example, they are not limited to, but typically include pRK5 (European Patent No. 307,247), pSV16B (PCT Publication No. 91/08291) and pVL1392 (PharMingen). The plasmid expression vector containing the said polynucleotide may be introduced into target cells by any method known in the art, including, but not limited to, transient transfection, microinjection, transduction, cell fusion, calcium phosphate precipitation, liposome-mediated transfection, DEAE dextran-mediated transfection, polybrene-mediated transfection, electroporation, gene gun methods, and other known methods for introducing DNA into cells (Wu et al., *J. Bio. Chem.,* 267:963-967, 1992; Wu and Wu, *J. Bio. Chem.,* 263:14621-14624, 1988).

In addition, virus expression vectors containing the said polynucleotide include, but are not limited to, retrovirus, adenovirus, herpes virus, avipox virus and so on. The retroviral vector is so constructed that non-viral proteins can be produced within the infected cells by the viral vector in which virus genes are all removed or modified. The main advantages of the retroviral vector for gene therapy are that it transfers a large amount of genes into replicative cells, precisely integrates the transferred genes into cellular DNA, and does not induce continuous infections after gene transfection (Miller, A. D., *Nature,* 357:455-460, 1992). The retroviral vector approved by FDA was prepared using PA317 amphotropic retrovirus packaging cells (Miller, A. D.

and Buttimore, C., *Molec. Cell Biol.,* 6:2895-2902, 1986). Non-retroviral vectors include adenovirus as described above (Rosenfeld et al., *Cell,* 68:143-155, 1992; Jaffe et al., *Nature Genetics,* 1:372-378, 1992; Lemarchand et al., *Proc. Natl. Acad. Sci. USA,* 89:6482-6486, 1992). The main advantages of adenovirus are that it transfers a large amount of DNA fragments (36 kb genomes) and is capable of infecting non-replicative cells at a very high titer. Moreover, herpes virus may also be useful for human genetic therapy (Wolfe, J. H., et al., Nature Genetics, 1:379-384, 1992). Besides, other known suitable viral vectors can be used.

In addition, a vector capable of inhibiting expressing the expression of KRS may be administered by a known method. For example, the vector may be administered locally, parenterally, orally, intranasally, intravenously, intramuscularly or subcutaneously, or by other suitable routes. Particularly, the vector may be injected directly into a target cancer or tumor cell at an effective amount for treating the tumor cell of a target tissue. Particularly for a cancer or tumor present in a body cavity such as in the eye, gastrointestinal tract, genitourinary tract, pulmonary and bronchial system and so on, the inventive pharmaceutical composition can be injected directly into the hollow organ affected by the cancer or tumor using a needle, a catheter or other delivery tubes. Any effective imaging device, such as X-ray, sonogram, or fiberoptic visualization system, may be used to locate the target tissue and guide the needle or catheter tube. In addition, the inventive pharmaceutical composition may be administered into the blood circulation system for treatment of a cancer or tumor which cannot be directly reached or anatomically isolated.

The present invention also provides a method for screening an agent which modulates cancer metastasis or cancer cell migration comprising:

(a) contacting a testing agent with KRS in the presence of the testing agent;

(b) measuring activity of KRS and selecting a testing agent which changes activity of KRS; and (c) testing whether the selected agent regulates tumor metastasis or cancer cell migration Various biochemical and molecular biology techniques or assays well known in the art can be employed to practice the present invention. Such techniques are described in, e.g., Sambrook et al., Molecular Cloning: A Laboratory Manual, Cold Spring Harbor Press, N.Y., Second (1989) and Third (2000) Editions; and Ausubel et al., Current Protocols in Molecular Biology, John Wiley & Sons, Inc., New York (1987-1999).

Preferably, the test agent is first assayed for their ability to modulate a biological activity of KRS (the first assay step). Particularly, in the first step, modulating agents that modulate a biological activity of an the said polypeptide may be identified by assaying a biological activity of isolated KRS in the presence of a test agent. More preferably, the present invention may comprise:

(a) contacting test agents with KRS in the presence of a test agent; and (b) measuring activity of KRS and selecting a testing agent which changes activity of KRS.

Modulation of different biological activities of KRS can be assayed in the first step. For example, a test agent can be assayed for activity to modulate expression level of KRS, e.g., transcription or translation. The test agent can also be assayed for activities in modulating cellular level or stability of KRS, e.g., post-translational modification or proteolysis.

Test agents that increase a biological activity of KRS by the first assay step are identified, the test agents are then subject to further testing for ability to modulate an activity of laminin receptor (67LR), in the presence of KRS (the second testing step). For example, the test agents are then subject to further testing for ability to modulate cancer metastasis or tumor cell migration.

As noted above, the KRS-modulating agents identified by the present invention can modulate cancer metastasis or tumor cell migration. If a test agent identified in the first testing step modulates cellular level (e.g., by altering transcription activity) of the KRS-modulating agents, it would modulate cancer metastasis or tumor cell migration.

On the other hand, if a test agent modulates an activity other than cellular level of KRS, then the further testing step is needed to confirm that their modulatory effect on the KRS would indeed lead to modulation of cancer metastasis or tumor cell migration. For example, a test agent, which modulates phosphorylation activity of KRS, needs to be further tested in order to confirm that modulation of phosphorylation activity of KRS can result in modulation of cancer metastasis or tumor cell migration.

In both the first step and the second step, an intact KRS and subunits or their fragments, analogs, or functional derivatives can be used. The fragments that can be employed in these assays usually retain one or more of the biological activities of KRS. Preferably, AIMP2 fragments may comprise $1^{st}$-$72^{nd}$ amino acid residues of SEQ. ID NO: 1. And fusion proteins containing such fragments or analogs can also be used for the screening of test agents. Functional derivatives of KRS usually have amino acid deletions and/or insertions and/or substitutions while maintaining one or more of the bioactivities and therefore can also be used in practicing the screening methods of the present invention.

A variety of the well-known techniques can be used to identify test agents that modulate KRS. Preferably, the test agents are screened with a cell based assay system. For example, in a typical cell based assay (i.e., the second screening step), activity of the reporter gene (i.e., enzyme activity) is measured in the presence of test agent, and then compared the activity of the reporter gene in the absence of test agent. The reporter gene can encode any detectable polypeptide (response or reporter polypeptide) known in the art, e.g., detectable by fluorescence or phosphorescence or by virtue of its possessing an enzymatic activity. The detectable response polypeptide can be, e.g., luciferase, alpha-glucuronidase, alpha-galactosidase, chloramphenicol acetyl transferase, green fluorescent protein, enhanced green fluorescent protein, and the human secreted alkaline phosphatase.

In the cell-based assays, the test agent (e.g., a peptide or a polypeptide) can also be expressed from a different vector that is also present in the host cell. In some methods, a library of test agents is encoded by a library of such vectors (e.g., a cDNA library; see the Example below). Such libraries can be generated using methods well known in the art (see, e.g., Sambrook et al. and Ausubel et al., supra) or obtained from a variety of commercial sources.

In addition to cell based assays described above, it can also be screened with non-cell based methods. These methods include, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel et al., supra (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin, *Am. J. Hum. Genet.,* 59:561-569, 1996; Tang, *Biochemistry,* 35:8216-8225, 1996; Lingner, *Proc. Natl. Acad. Sci. U.S.A.,* 93:10712, 1996; and Chodosh, *Mol. Cell. Biol.,* 6:4723-4733, 1986.

First Assay Step: Screening Test Agents that Modulate KRS

A number of assay systems can be employed to screen test agents for modulators of KRS. As noted above, the screening can utilize an in vitro assay system or a cell-based assay system. In this screening step, test agents can be screened for binding to KRS, altering cellular level of KRS, or modulating other biological activities of KRS.

1) Screening of Test Agents that Bind KRS

In the first screening step some methods, binding of a test agent to KRS is determined. For example, it can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to KRS, e.g., co-immunoprecipitation with KRS by an antibody directed to KRS. The test agent can also be identified by detecting a signal that indicates that the agent binds to KRS, e.g., fluorescence quenching.

Competition assays provide a suitable format for identifying test agents that specifically bind to KRS. In such formats, test agents are screened in competition with a compound already known to bind to KRS. The known binding compound can be a synthetic compound. It can also be an antibody, which specifically recognizes KRS polypeptide, e.g., a monoclonal antibody directed against KRS. If the test agent inhibits binding of the compound known to bind KRS, then the test agent also binds KRS.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using .sup.125I label (see Morel et al., Mol. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize KRS or its fragments onto a solid phase matrix. The solid phase matrix is then put in contact with test agents, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing KRS, the test agents are bound to the solid matrix and the KRS is then added.

Soluble assays include some of the combinatory libraries screening methods described above. Under the soluble assay formats, neither the test agents nor KRS are bound to a solid support. Binding of KRS or fragment thereof to a test agent can be determined by, e.g., changes in fluorescence of either KRS or the test agents, or both. Fluorescence may be intrinsic or conferred by labeling either component with a fluorophor.

In some binding assays, either KRS, the test agent, or a third molecule (e.g., an antibody against KRS) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}I$, $^{32}P$, $^{35}S$) or a chemiluminescent or fluorescent group. Similarly, the detectable group can be a substrate, cofactor, inhibitor or affinity ligand.

2) Screening Test Agents Modulating Other Activities of KRS

Binding of a test agent to KRS provides an indication that the agent can be a modulator of KRS. It also suggests that the agent may modulate activity of laminin receptor to modulate cancer metastasis or tumor cell migration. Thus, a test agent that binds to KRS can be further tested for ability to modulate activity of laminin receptor Alternatively, a test agent that binds to KRS can be further examined to determine its activity on KRS. The existence, nature, and extent of such activity can be tested by an activity assay. Such an activity assay can confirm that the test agent binding to KRS indeed has a modulatory activity on KRS. More often, such activity assays can be used independently to identify test agents that modulate activities of KRS (i.e., without first assaying their ability to bind to KRS). In general, such methods involve adding a test agent to a sample containing KRS in the presence or absence of other molecules or reagents which are necessary to test a biological activity of KRS and determining an alteration in the biological activity of KRS. In addition to assays for screening agents that modulate enzymatic or other biological activities of KRS, the activity assays also encompass in vitro screening and in vivo screening for alterations in expression or cellular level of KRS.

Second Test Step: Screening Agents that Modulate Tumor Metastasis or Tumor Cell Migration Once a modulating agent has been identified to bind to KRS and/or to modulate a biological activity (including cellular level) of KRS, it can be further tested for ability to modulate tumor metastasis or tumor cell migration. Modulation of tumor metastasis or tumor cell migration by the modulating agent is typically tested in the presence of KRS. When a cell-based screening system is employed, KRS can be expressed from an expression vector that has been introduced into a host cell. Alternatively, KRS can be supplied endogenously by the host cell in the screening system.

The present invention also provides a method for screening an agent inhibiting an interaction between KRS and 67LR comprising:

(a) contacting a testing agent with KRS and laminin receptor (67LR) in the presence of the testing agent; and (b) testing whether the selected agent regulates an interaction between KRS and laminin receptor.

The said agent can be the things which stimulates or reinforce interaction between KRS and laminin receptor (67LR), or in contrary, it can be the things which inhibits or aggravates the interaction.

The (b) step can comprise detecting a relative change of the interaction level between KRS and 67LR polypeptide in the cell or the cell lysate thereof contacting the test agent compared to the interaction level between KRS and 67LR in the cell or the cell lysate thereof without contacting the test agent.

The method for identifying can be performed by any conventional method known in the art such as labeled in vitro protein-protein binding assays (in vitro full-down assays), EMSA (electrophoretic mobility shift assays), immunoassays for protein binding, functional assays (phosphorylation assays, etc.), yeast two hybrid assay, assays of non-immune immunoprecipitations, Immunoprecipitation/The present inventorsstern blotting assays, immuno-co-localization assays.

For example, yeast two hybrid analyses may be carried out using yeast expressing AIMP2 and p53, or parts or homologues of the proteins, fused with the DNA-binding domain of bacteria repressor LexA or yeast GAL4 and the transactivation domain of yeast GAL4 protein, respectively (Kim, M. J. et al., *Nat. Gent.,* 34:330-336, 2003). The interaction between AIMP2 and p53 reconstructs a transactivator inducing the expression of a reporter gene under the control by a promoter having a regulatory sequence binding to the DNA-binding domain of LexA or GAL4.

As described above, the reporter gene may be any gene known in the art encoding a detectable polypeptide. For example, chloramphenicol acetyltransferase (CAT), luciferase, β-galactosidase, β-glucosidase, alkaline phosphatase, green fluorescent protein (GFP), etc. may be used. If the interaction between AIMP2 and p53, or parts or homologues of the proteins is facilitated or enhance by a test agent, the expression of the reporter gene increases than under a normal condition. Conversely, if the interaction is inhibited or reduced by a test agent, the reporter gene is not expressed or expressed less than under a normal condition.

Further, a reporter gene encoding a protein which enables growth of yeast (i.e., if the reporter gene is not expressed, the growth of yeast is inhibited) may be selected. For example, auxotropic genes encoding enzymes involved in biosynthesis for obtaining amino acids or nitrogenous bases (e.g., yeast genes such as ADE3, HISS, etc. or similar genes from other species) may be used. If the expression of AIMP2 and p53, or parts or homologues of the proteins is inhibited or reduced by a test agent, the reporter gene is not expressed or less expressed. Accordingly, under such a condition, the growth of yeast is stopped or retarded. Such an effect on the expression of the reporter gene may be observed with eyes or using devices (e.g., a microscope).

In addition, as results of analyzing overexpression of 67LR and KRS performed to lung cancer or breast cancer patients, it is found that, relationship between overexpression of KRS and lung cancer or breast cancer is high in case of 67LR is over-expressed (table 1). Accordingly, the present invention provides a method for diagnosis of lung cancer or breast cancer consisting of:

(a) analyzing overexpression of 67LR in a sample; and (b) analyzing overexpression of LRS in the 67LR over-expressed sample.

Sampling for diagnosis and treatment for diagnosis and analysis of over-expression of 67LR and KRS may use molecular biological techniques which are well known in the art and those are well described above.

Hereafter, the figures of the present invention will be described.

FIGS. 1 to 6 show specific interaction between human KRS and laminin receptor. In FIG. 1, the interaction between full-length human KRS and 37LRP/p40 was determined by yeast two hybrid assay. AIMP1 and AIMP2, the two components of the multi-ARS complex, were used as positive and negative control, respectively. The positive interaction is indicated by blue colony formation on yeast medium containing X-gal. In FIG. 2, 37LRP was synthesized by in vitro translation in the presence of [$^{35}$S] methionine and subjected to pull-down with GST-KRS or GST. 37LRP co-precipitated with GST-KRS was detected by autoradiography. In FIG. 3, The peptide regions of KRS and 37LRP involved in their interaction was determined by yeast two hybrid assay as above. 37LRP contains 296 amino acids in which the N-terminal cytoplasmic (amino acids 54-113) and C-terminal extracellular (amino acids 137-210) domains are divided by transmembrane domain (amino acids 113-137). The N-terminal unique extension (about 70 amino acids) of human KRS (597 amino acids) is followed by OB-fold anticodon-binding (amino acids 70-214) and catalytic domains (amino acids 220-574). In FIG. 4, A549 cells transfected with Myc-KRS were lyzed and subjected to immunoblot analysis with anti-Myc and anti-laminin receptor antibodies. Myc-KRS was immunoprecipitated with anti-Myc antibody and co-precipitated 67LR and 37LRP were determined by immunoblotting. For the specific blotting of 37LRP and 67LR, the present inventors used polyclonal antibodies, H-141 and F-18 (Santacruz), respectively (WCL: whole cell lysate). In FIG. 5, the lysates of Myc-KRS transfected A549 cells were subjected to Western blotting with the indicated antibodies. The cells were separated to cytoplasmic and membrane fractions and immunoprecipitated with anti-Myc antibody and co-precipitation of 37LRP and 67LR was determined by Western blotting. IgG was used as control. In FIG. 6, when treated with 10 ug/ml of laminin for 1 hr, the present inventors confirmed that the binding of 67LR and KRS was increased. To identify it, immunoprecipitation was performed with 67LR recognizing antibody (abcam, cat #ab2508), and the IgG level of the left is total IgG from a rabbit and was used as control. After SDS PAGE was performed, then was moved to PVDF membrane, and was performed immuno blot with KRS and 67LR recognizing antibody respectively.

FIGS. 7 to 12 show that laminin-induced membrane translocation and phosphorylation of KRS. In FIG. 7, A549 cells were treated with laminin (10 ug/ml) and the level of 67LR, 37LRP and KRS was determined by Western blotting at the indicated times. Hsp90 and Cadherin were used as markers for cytoplasm and membrane, respectively. In FIG. 8, A549 cells untreated or treated with laminin for 1 h were subjected to immunofluorescence staining with anti-67LR (MLuC5, Santacruz, sc-59732) (red) and -KRS antibodies (green). In FIG. 9, A549 cells were treated with U73122 (U), staurosporin (ST) and LY294002 (LY) that inhibit PLC-gamma, PKC and PI3K, respectively, for 3 hr, then with laminin for 1 hr and checked how these kinase inhibitors would affect the membrane and cytoplasmic level of 67LR and KRS. In FIG. 10, A549 cells were transfected with Myc-KRS and incubated for 24 h. The cells were treated with the indicated chemicals and then with laminin as above. Myc-KRS was immunoprecipitated, and immunoblotted with anti-p-Thr, -Ser, and -Tyr antibodies. In FIG. 11, A549 cells were transfected with Myc-KRS and cultivated for 24 hr. The transfectants were pre-treated with LY294002 for 3 hr and then treated with laminin for 1 h. Myc-KRS was immunoprecipitated and co-precipitation of 67LR was determined by Western blotting. IgG was used as a control for immunoprecipitation. In FIG. 12, A549 cells were cultivated in the absence and presence of laminin and LY294002 as indicated. EPRS (glutamyl-prolyl-tRNA synthetase) was immunoprecipitated with its specific antibody (AbCam), and co-immunoprecipitation of KRS was determined by Western blotting (upper). The immune-depleted supernatant (ID) were subjected to Western blottingting with anti-KRS and -EPRS antibodies.

FIGS. 13 to 17 show that KRS stabilizes membrane-bound 67LR. In FIG. 13, A549 cells were transfected with si-control or si-KRS and incubated in the absence and presence of laminin. The cells were then separated to cytoplasm and membrane fractions, and the levels of 67LR and KRS in each fraction were determined by Western blotting. Cadherin (cad) and hsp90 were used as the markers for plasma membrane and cytoplasm, respectively. In FIG. 14, the membrane-bound 67LR level in A549 cells was monitored by flow cytometry using anti-LR antibody (MLuC5). The cells were transfected with empty vector or KRS plasmid and incubated for 24 h (upper). To see the effect of KRS suppression on 67LR level, the cells were transfected with si-KRS or si-control and incubated for 48 h (lower). In FIG. 15, A549 cells transfected with EV or KRS was selected with G418 for a week and cellular distribution of 67LR was determined by immunofluorescence staining with anti-LR antibody (MLuC5). The membrane-located LR was highlighted with white arrows. In FIG. 16, A549 cells were treated with cycloheximide to inhibit de novo protein synthesis and the effect of KRS levels on 67LR level in membrane and cytoplasm was determined by Western blotting. In FIG. 17, the importance of KRS for cellular stability of 67LR was determined by pulse-chase experiment. 293 cells were transfected with si-KRS or si-control and radioactive methionine was incorporated for 1 h. 67LR was immunoprecipitated with antibody specifically recognizing 67LR (F-18, Santacruz), separated by SDS-PAGE and autoradiographed. Suppression of KRS with its specific siRNA was confirmed by Western blotting and tubulin is a loading control.

FIGS. 18 to 22 show that KRS enhances cell migration and cancer metastasis via 67LR. In FIG. 18, A549 cells were transfected with the indicated plasmids, incubated in the absence and presence of laminin and their effect on cell migration was determined by measuring the migrated cells in transwell chamber as described. The numbers of the cells passed through the membrane were counted and shown in each panel. The experiments were performed three times. In FIG. 19, the cells treated as above were used to determine MMP-2 activity and level by zymography and Western blotting, respectively. In FIG. 20, Breast carcinoma 4T-1 cells were transfected with the indicated siRNA and subcutaneously injected to the back of Balb/C mice. After 21 days, mouse lungs were isolated and tumor nodules over 1 mm in diameter were counted. In FIG. 21, two different 4T-1 cells stably expressing exogenously introduced KRS (KRS-1 and -2) were also inoculated as above and the tumor nodules were counted 30 days after injection. 4T-1 cells with empty vector were used as control. In FIG. 22, expression levels of KRS and 67LR in lung (upper) and breast (lower) cancer tissues were compared by immunohistochemical staining with their respective antibodies. 39 lung and 40 breast cancer tissues were subjected to immunohistochemical staining with anti-KRS and anti-67LR antibodies and their expression levels were compared with those in normal tissues (9 samples for each tissue). Shown here are the representative pairs of the same cancer patients demonstrating the overexpression of KRS and 67LR. The result of statistical analysis for the correlation between KRS and 67LR level is shown in table 1.

FIG. 23 shows membrane level of 67LR depends on KRS expression. 293 cells transfected with the indicated plasmids were separated to cytoplasmic and membrane fractions, and the levels of 67LR, 37LRP and KRS in each fraction were determined by Western blotting with the corresponding antibodies.

FIGS. 24 to 27 show effect of intracellular and extracellular KRS on cell migration, protein synthesis and cell cycle. In FIG. 24, Migration of A549 cells incubated in the absence of laminin was determined was determined by measuring the migrated cells in Transwell chamber. In FIG. 25, to see the chemotactic activity of KRS, the serum-free medium containing the indicated KRS concentration was placed in the lower chamber and A549 cells were incubated in the upper chamber in Transwell chamber. After 6 hr of incubation, the migrant were counted. In FIG. 26, KRS level in A549 cells was down- and up-regulated by introduction of siRNA and exogenous KRS (lower panels of FIGS. 26 and 27). The transfected cells were incubated for 48 and 24 hr, respectively and starved in methionine-free medium for 1 hr and radioactively labeled methionine was incorporated for 2 hr. After washing, the cells were incubated for 4 h and lyzed in 0.5% triton X-100 lysis solution, and incorporated radioactivity was determined by liquid scintillation counting. In FIG. 27, A549 cells transfected as indicated were fixed and stained with propidium iodide, and their cell cycle was determined by flow cytometry.

FIGS. 28 to 30 show the effect of KRS suppression on cancer metastasis. In FIG. 28, the effect of si-KRS and -DRS on the expression of their target proteins was determined by Western blotting. Tubulin was used as loading control. In FIG. 29, the siRNA transfected cells ($1\times10^6$) were injected as described in methods and the effect of KRS and DRS suppression on primary tumor growth was determined by measuring tumor weight and volumes 21 days after inoculation. Each group contained 5 mice. In FIG. 30, the lungs isolated above were fixed in 10% formalin. The number and size of metastatic tumor nodules were shown.

FIGS. 31 to 33 show the effect of KRS overexpression on cancer metastasis. In FIG. 31, overexpression of KRS-1 and -2 cell lines was determined by Western blotting. In FIG. 32, the effect of KRS overexpression on primary tumor growth was also compared as above. In FIG. 33, the effect of KRS overexpression on cancer metastasis was determined 30 days after inoculation. Each group contained 4 mice.

MODE FOR INVENTION

Figure 1:
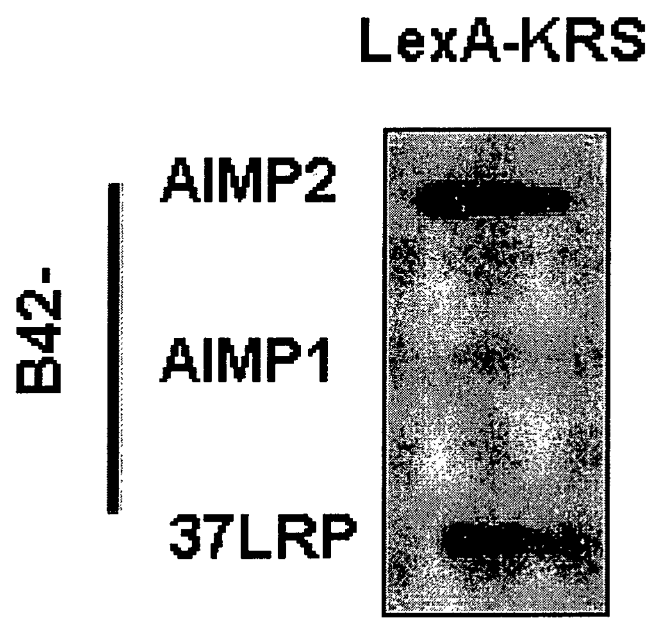
FIG. 1 is the result confirming the interaction between human KRS and 37LRP/p40 using yeast two hybrid assay.

Hereinafter, the present invention will be described in detail by examples. It is to be understood, however, that these examples are for illustrative purpose only and are not constructed to limit the scope of the present invention.

<Experimental Method>

1. Cell Culture and Materials

A549 and HEK293 were purchased from ATCC. Mouse mammary carcinoma 4T-1 cell line was kindly provided by Dr. Seong Jin Kim (Gachun Medical School). RPMI (for A549 and 4T-1 cells) and Dulbecco's Modified Eagle Medium (for the other cell lines), containing 10% fetal bovine serum and 1% antibiotics were used for cell cultivation. pcDNA3.1 encoding 37LRP was a kind gift from Dr. Hirofumi Tachibana (Kyushu University). Myc-tagged human KRS and DRS were cloned at the EcoRI/XhoI site of pcDNA3. Murine KRS cDNA was obtained by RT-PCR and cloned at HindIII/XhoI site of pcDNA3.1. siRNAs targeting murine and human KRS and DRS were purchased from Invitrogen. Sequences for siRNAs would be provided upon request. Gene porter (GTS) and Lipofectamine 2000 (Invitrogen) were used as transfection reagent. LY294002, U73122 and staurosporin were purchased from Calbiochem, and cycloheximide and laminin (Engelbreth-Holm-Swarm murine sarcoma) from Sigma.

2. Immunoprecipitation and the Present Inventorsstern Blot.

The cells were lysed with 20 mM Tris-HCl (pH 7.4) buffer containing 150 mM NaCl, 0.5% TritonX-100, 0.1% SDS, and protease inhibitor. The protein extracts were incubated with normal IgG and protein G agarose for 2 hr and then centrifuged to remove nonspecific IgG binding proteins. The present inventors then mixed the supernatants with purified 67LR antibody (F-18, Santacruz), incubated for 2 hr at 4° C. with agitation, and added protein A agarose. After washing three times with the ice-cold lysis buffer, the precipitates were dissolved in the SDS sample buffer and separated by SDS-PAGE. To determine the binding of KRS and LR in different cell fractions, the present inventors transfected pcDNA3.1-Myc-KRS and separated the plasma membrane and cytoplasmic fractions using the proteoextract kit (Calbiochem) following the manufacturer's instruction, and co-immunoprecipitation was performed as above. To analyze protein levels, the proteins extracted from the cells were separated by 10% SDS-PAGE. Anti-LR antibody (Abcam, ab2508) was used for simultaneous immunoblotting of 37LRP and 67LR unless specified. Antibodies for hsp90 and Pan-cadherin were purchased from Santacruz.

3. Flow Cytometry

To address cell cycle, the cultivated cells were transfected or treated with the indicated vector or chemicals, fixed with 70% ethanol for 1 hr at 4° C. and washed with ice-cold PBS two times. The cells were then stained with propidium iodide (50 ug/ml), sodium citrate 0.1%, NP40 0.3% and RNaseA (50 ug/ml) for 40 min and subjected to flow cytometry (FACS Calibur, Beckton-Dickinson). For each sample, 20,000 cells were analyzed using Cell Quest Pro software. For analysis of amount of 67 kD LR on cell surface, $1\times10^6$ cells were incubated IgG or anti-LR antibody (MLuC5 1 ug) recognizing extracellular domain of 67LR and then with FITC secondary antibody. After washing with PBS, the samples were scanned by FACS.

4. Immunofluorescent and Immunohistochemical Staining

A549 cells on a 9 mm cover slip were fixed with 70% methyl alcohol and washed briefly with cold phosphate buffer saline (PBS). After incubation with blocking buffer containing 1% CAS, 3% BSA and 0.5% tritonX-100 for 30 min, the cells were incubated with antibody against KRS (Abcam), and MLuC-5 (Santacruz) for 1 hr. Alexa488 and 568 (Invitrogen) were then added for 30 min at room temperature. After washing with cold PBS for 30 min, specimens were observed by laser-scanning microscopy. The tissue array slides for breast and lung cancer were purchased from Super-Biochip (Korea) and subjected to immunohistochemical staining to determine the expression level of 67LR and KRS with their respective antibodies as described (Park, S. G. et al. Human lysyl-tRNA synthetase is secreted to trigger pro-inflammatory response, *Proc. Natl. Acad. Sci. USA* 102, 6356-6361 (2005)). Statistical analyses were performed using the Pearson $X^2$ test and Student t test to evaluate the correlation between 67LR and KRS expression. P values<0.05 were considered significant. All statistical analyses were performed using SPSS v11.5 software (SPSS, Chicago, Ill.).

5. Pulse-Chase Experiment 293 cells were transfected with si-KRS or si-control (Invitrogen) using lipofectamine 2000. The cells were then incubated with methionine-free medium for 1 hr, and [$^{35}$S] methionine (50 Ci/ml) was added and incubated for 1 h. After washing off the radioactive methionine with fresh medium, 67LR was immunoprecipitated with its specific antibody (Santacruz), separated by 12% SDS-PAGE and subjected to autoradiagraphy using BAS (FLA-3000, Fuji-Film). The amount of 67LR was quantified by Multi-gauge program (V3.0, FujiFilm).

6. Yeast Two Hybrid Analysis cDNAs encoding different fragments of human KRS were obtained by PCR with the corresponding primers. The PCR product for KRS was digested with EcoRI and XhoI, and ligated the corresponding sites of pEG202 (for the construction of LexA-fusion proteins) and pJG4-5 (for the construction of B42-fusion proteins). The cDNAs encoding 37LRP fragments were kindly provided from Dr. Barbara J. Ballermann (University of Alberta), and they were subcloned at EcoRI and XhoI sites of pJG4-5. The interactions between the two fusion protein series were analyzed by the formation of blue colonies on the X-gal-containing yeast medium.

7. In vitro Binding Assay.

The present inventors expressed GST-KRS or GST in *Escherichia coli* Rosetta (DE3) strain, mixed the protein extracts with glutathione-Sepharose in the PBS buffer containing 1% Triton X-100 and 0.5% N-laurylsarcosine at 4° C. for 2 h. The present inventors synthesized human 37LRP by in vitro translation in the presence of [$^{35}$S] methionine using pcDNA3-37LRP as the template using TNT Quick coupled Transcription/Translation system (Promega). The synthesized 37LRP was added to the GST protein mixtures above, incubated at 4° C. for 4 hr with rotation in the PBS buffer containing 1% Triton X-100, 0.5% N-laurylsarcosine, 1 mM DTT, 2 mM EDTA and 300 M phenylmethylsulfonyl fluoride, and washed six times with the same buffer containing 0.5% Triton X-100. The present inventors then eluted the proteins bound to Sepharose beads with the SDS sample buffer, separated by SDS-PAGE and autoradiographed.

8. Cell Migration Assay

Cell migration was determined by using 24-Transwell chambers with polycarbonate membranes (8.0 um pore size, Costar) as previously described (Park, S. G. et al. Human lysyl-tRNA synthetase is secreted to trigger pro-inflammatory response, *Proc. Natl. Acad. Sci. USA* 102, 6356-6361 (2005)). A549 cells were suspended in serum-free RPMI and added to the upper chamber at $1\times10^5$ cells per well. Each of the purified human KRS at the indicated concentrations, laminin (10 μg/ml) or gelatin (10 μg/ml) was placed in the lower well, and the cells were allowed to migrate for 6 hr at 37° C. in $CO_2$ incubator. The cells were fixed with 70% methyl alcohol in PBS for 30 min and washed with PBS three times. The cells were stained with hematoxylin (Sigma) for 10 min and washed with distilled water. The non-migrant cells were removed from the upper face of the membrane with a cotton swab. The membranes were excised from the chamber and mounted with Gel Mount (Biomeda, Foster City, Calif.). The migrant cells (those attached to the lower face of the membrane) were counted at four randomly selected scopes in high power fields (×20).

9. Zymography

A549 cells transfected with the plasmids encoding the indicated siRNAs and recombinant KRS (or DRS) were incubated for 48 and 24 hr, respectively, and were seeded ($1\times10^5$ cells/well) in RPMI containing 10% FBS. After starving the cells in serum-free RPMI for 2 hr, laminin was added and incubated for 24 hr at 10 μg/ml. 20 l of the culture medium was mixed with 5×FOD buffer (0.125M Tris-HCl, pH 6.8, containing 4% SDS, 20% glycerol and 0.01% bromophenol blue) and subjected to 10% SDS-PAGE containing 1 mg/ml of gelatin. The gel was washed with 2.5% Triton X-100 twice for each 20 min, then with distilled water twice for each 20 min and incubated with the reaction buffer (50 mM Tris-HCl, pH 7.5, containing 10 mM CaCl2, 150 mM NaCl, 1 M $ZnCl_2$, 1% Triton X-100, 0.002% sodium azide) for 24 h at 37° C. The gel was washed with distilled water and stained with Coomassie blue R250 and destained with 35% methanol.

10. Cancer Metastasis Experiment In Vivo

Mouse mammary carcinoma 4T-1 cells were transfected with si-KRS -DRS or si-control and incubated for 24 hr. The cells ($1\times10^6$) were subcutaneously inoculated into the back of 6-week old female Balb/c mice. The effect of siRNAs to their target expression was tested in the remaining cells 48 hr after transfection and also in the primary tumors from 3 to 10 days at 2 days intervals after inoculation by Western blotting with their corresponding antibodies. The growth of tumor was monitored by measuring tumor size three times weekly. The whole body weights were also measured at the same time. The mice were sacrificed 21 days after inoculation and the primary tumors and lungs were excised from the animals. The lungs were fixed in 10% formalin for twenty four hours. The number and size of metastatic tumor nodules on lungs were counted, and tumor nodules of larger than 1 mm in diameter were recorded separately. The primary tumors were also weighed. To examine the effect of KRS overexpression on cancer metastasis, murine KRS vector or empty vector were transfected into 4T-1 cells and stable transfectants were selected by the incubation in the presence of G418 for 3 weeks. The present inventors then picked up several single colonies and compared KRS expression level by Western blotting. Two different colonies (KRS-1 and -2) expressing KRS at higher level than the control cells were chosen and used for inoculation. All the procedures were performed as above except that the mice were sacrificed 30 days after inoculation.

<Experimental Result and Discussion>

Figure 2:
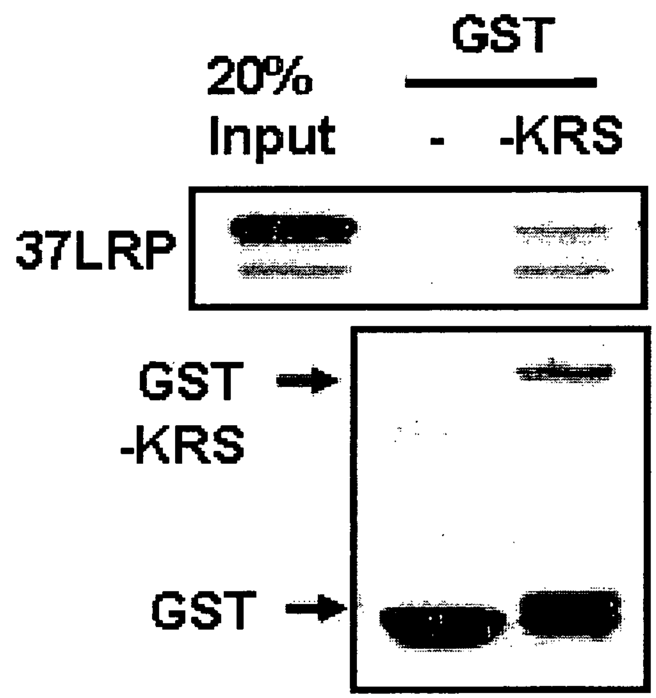
FIG. 2 is the result confirming the interaction between human KRS and 37LRP using pull-down assay.
Figure 3:
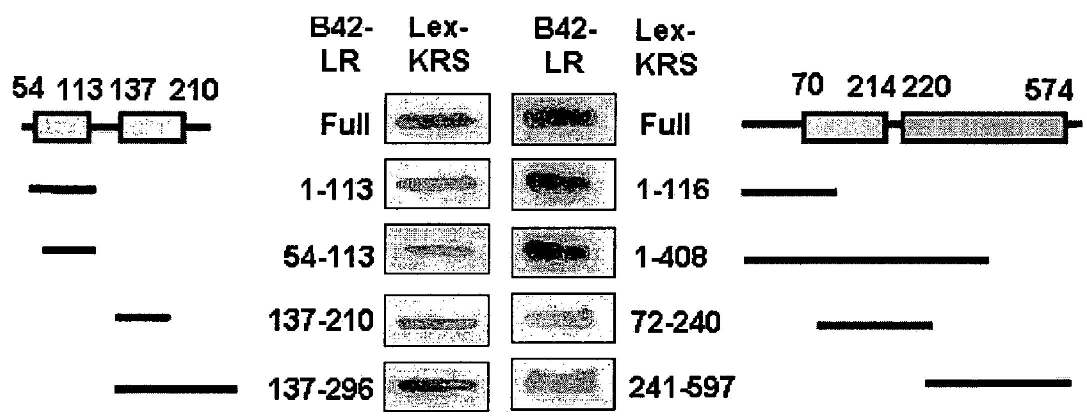
FIG. 3 is the result confirming the region of interaction between human KRS and 37LRP.

The specific interaction between full-length KRS and 37LRP was confirmed by yeast two hybrid assay. LexA-KRS generated blue colonies when paired with B42-37LRP as well as AIMP2, the known partner of KRS (Kim, J. Y. et al. p38 is essential for the assembly and stability of macromolecular tRNA synthetase complex: Implications for its physiological significance, *Proc. Natl. Acad. Sci. USA* 99, 7912-7916 (2002)), but not with AIMP1 (FIG. 1). For in vitro binding assay, [$^{35}$S] methionine-labelled 37LRP was mixed with either GST-KRS or GST, precipitated with glutathione-Sepharose and subjected to autoradiography. 37LRP was co-precipitated with GST-KRS, but not with GST (FIG. 2). Deletion mapping by yeast two hybrid assay determined that the N-terminal extension of human KRS and the C-terminal extracellular domain of LR are involved in their association (FIG. 3).

Figure 4:
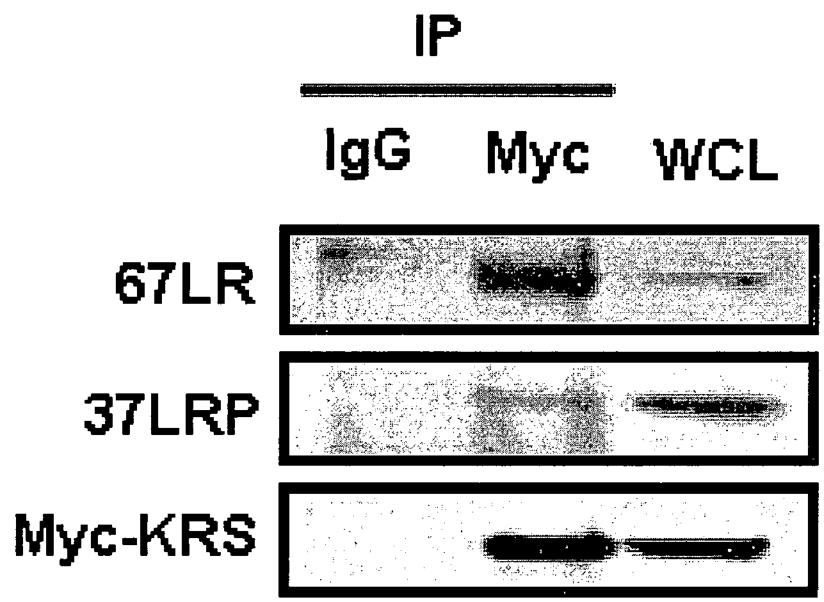
FIG. 4 is the result of immunoblot analysis to confirm the binding of KRS to 67LR and 37LRP in A549 cells transfected with Myc-KRS using anti-Myc and anti-laminin receptor antibodies.
Figure 5:
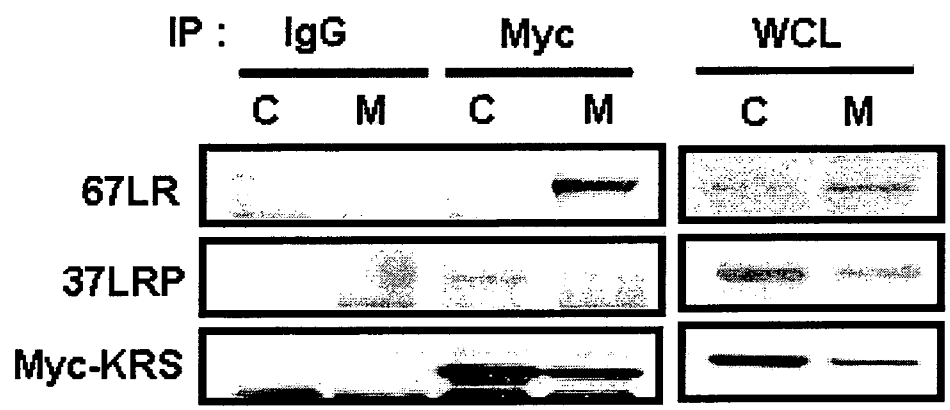
FIG. 5 is the result of Western blotting analysis to confirm the binding of KRS to 67LR and 37LRP in the lysates of Myc-KRS transfected A549 cells.
Figure 6:
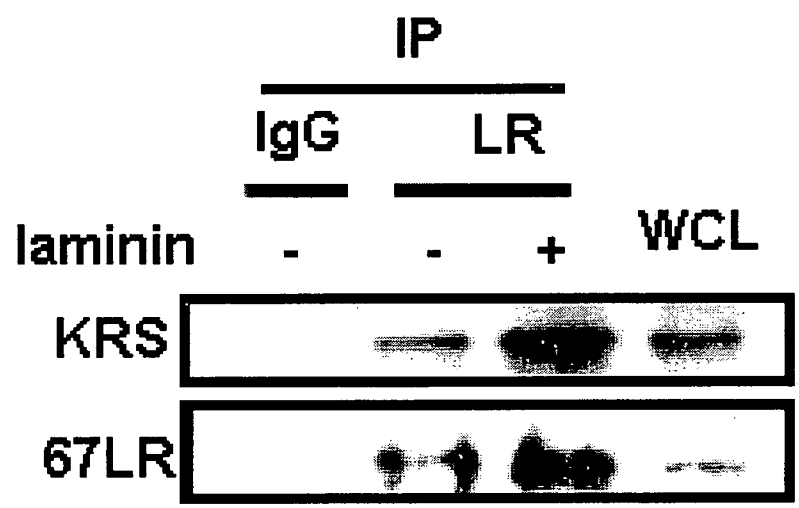
FIG. 6 is the result of immunoprecipitation to confirm the binding of 67LR and KRS depending on the treatment with laminin.

Since cytoplasmic 37LRP is converted to membrane-embedded 67LR, the present inventors checked whether KRS would bind differently between 37LPR and 67LR. Myc-KRS was introduced into lung carcinoma A549 cells and immunoprecipited with anti-Myc antibody. The present inventorsstern blotting of the whole cell lysate demonstrated that 67LR exists at lower level than 37LRP (FIG. 4 right). Nonetheless, Myc-KRS predominantly bound to 67LR than 37LRP (FIG. 4 left). The present inventors then separated A549 cells into cytoplasmic and plasma membrane fractions and determined the interaction of Myc-KRS with 67LR and 37LRP. 37LRP and 67LR were mainly detected at cytoplasm and plasma membrane, respectively (FIG. 5 right), while KRS existed at both fractions although a major portion was observed at cytoplasm. When both fractions were subjected to immunoprecipitation with anti-Myc antibody, the membrane-bound 67LR was mainly co-precipitated with KRS although low amount of 37LRP in cytoplasm was also precipitated (FIG. 5 left), indicating preferential interaction between membrane-resident 67LR and KRS.

Figure 7:
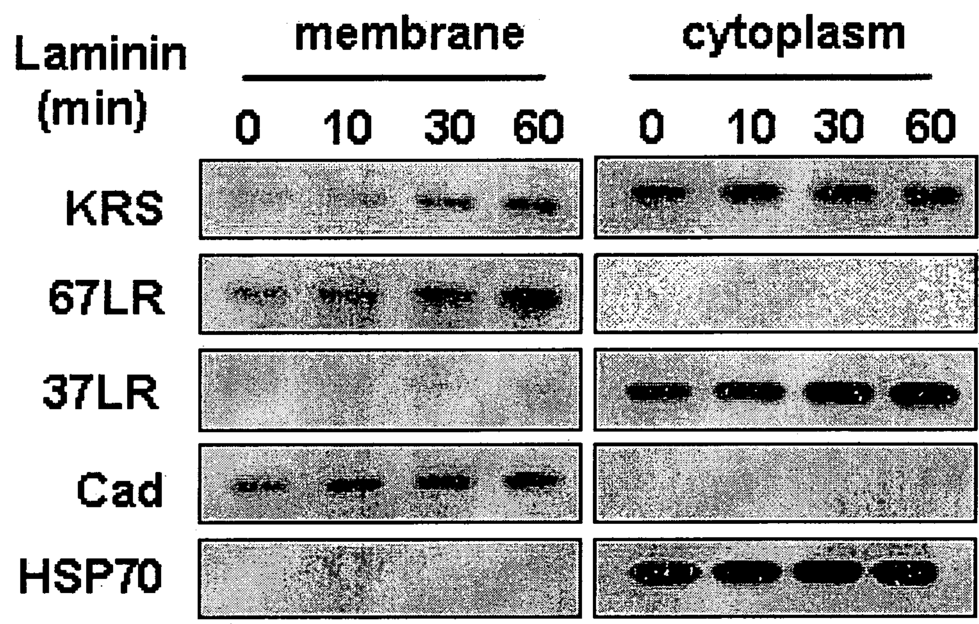
FIG. 7 is the result of Western blotting to confirm the level of 67LR, 37LRP and KRS depending on the treatment with laminin.
Figure 8:
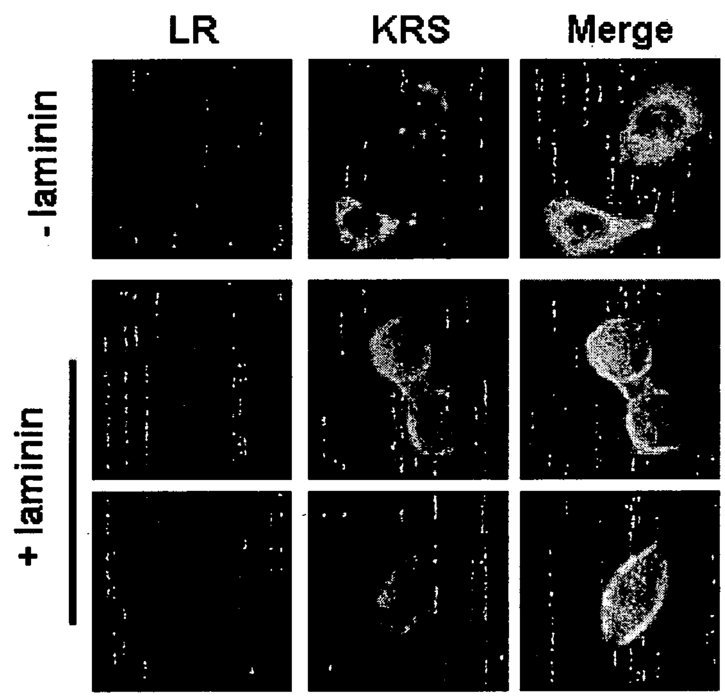
FIG. 8 is the result of immunofluorescence staining to examine an expression level of 67LR and KRS depending on the treatment with laminin in A549 cells.
Figure 9:
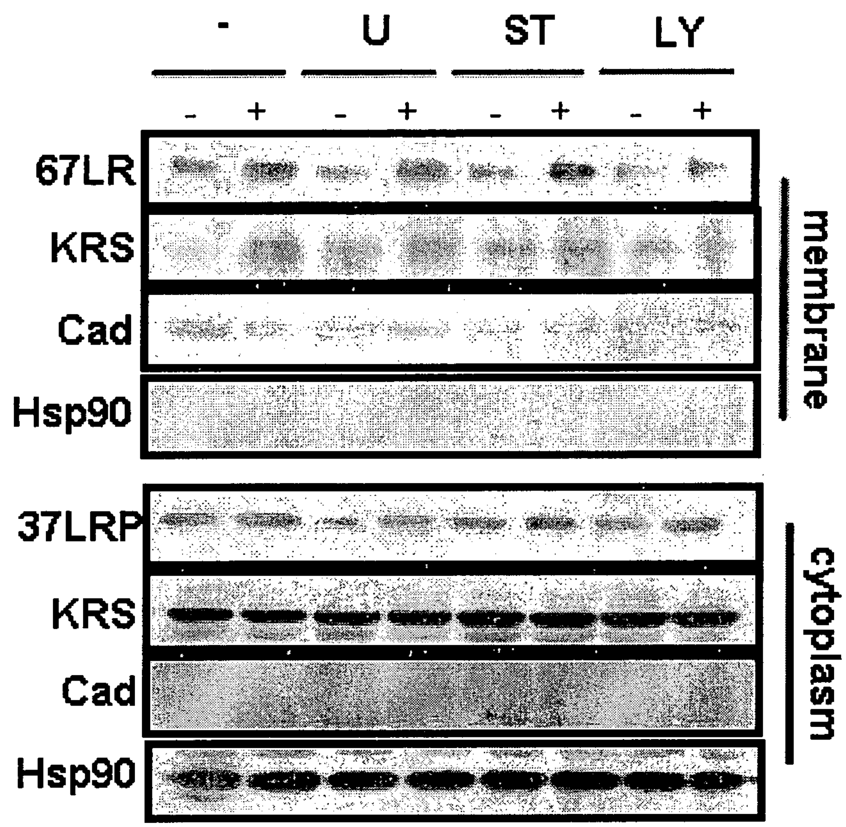
FIG. 9 is the result confirming the effect of kinase inhibitors on the membrane and cytoplasmic expression level of 67LR and KRS.
Figure 10:
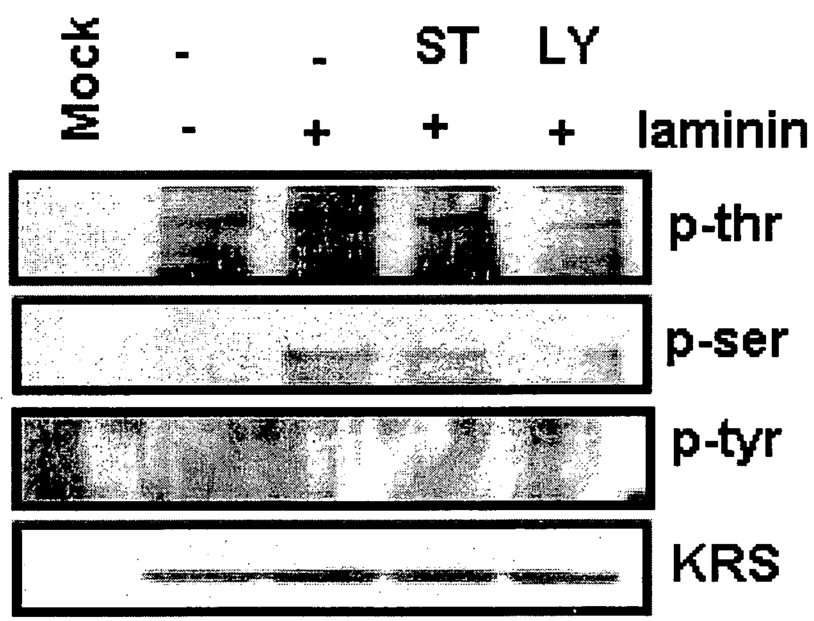
FIG. 10 is the result of immunoblot to measure the phosphorylation level in KRS expressing-A549 cell when laminin and kinase inhibitor were treated using anti-p-Thr, -Ser, and -Tyr antibodies about phosphorylation.
Figure 11:
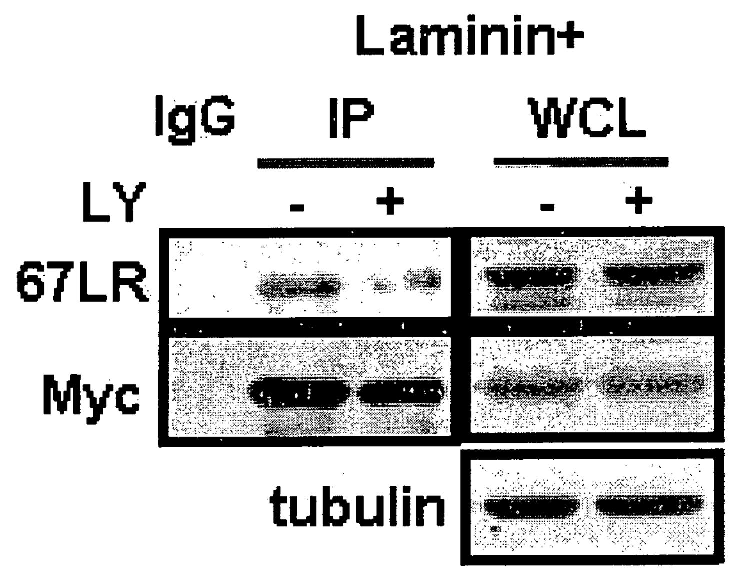
FIG. 11 is the result of Western blotting to determine the binding of phosphorylated KRS to 67LR in the KRS expressing A549 cells.
Figure 12:
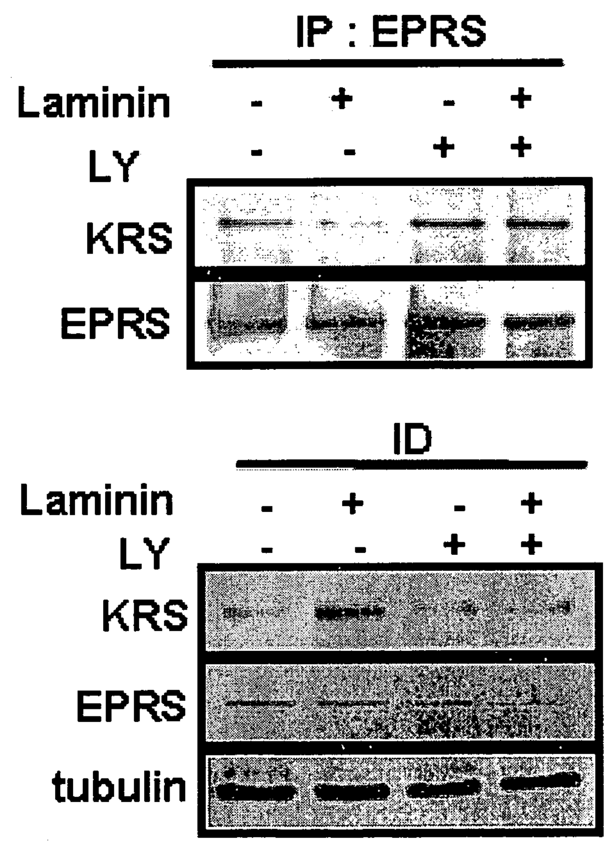
FIG. 12 is the result of Western blotting to confirm the effect of laminin on binding of KRS and EPRS.

The present inventors then investigated whether cellular distribution of KRS is changed by laminin treatment in A549 cells by cell fractionation and immunofluorescence staining. After laminin treatment, membrane level of KRS and 67LR was gradually increased with little changes in the cytoplasmic KRS and 37LRP level or their expression (FIG. 7 and data not shown). Immunofluorescence staining also demonstrated the shift of 67LR and KRS toward membrane side by laminin treatment (FIG. 8, red and green, respectively). The present inventors then investigated whether membrane translocation of KRS involves post-translational modification. A few different kinases such as phosphoinositide 3-0H kinase (PI3K)(Shaw, L. M., Rabinovitz, I., Wang, H. H., Toker, A. & Mericurio. A. M. Activation of phosphoinositide 3-0H kinase by the alpha6beta4 integrin promotes carcinoma invasion. *Cell* 91, 949-960 (1997)), protein kinase C (PKC)(Li, Y. Q. et al. Protein kinase C mediates the signal for interferon-gamma mRNA expression in cytotoxic T cells after their adhesion to laminin. *Immunology* 93, 455-461 (1998)) and phospholipase C-gamma (PLC-gamma)(Vossmeyer, D., Hofmann, W., Loster, K., Reutter, W. & Danker, K. Phospholipase C-gamma binds alpha1beta1 integrin and modulates alpha1beta1 integrin-specific adhesion. *J. Biol. Chem.* 277, 4636-4643 (2002); Kanner, S. B., Grosmaire, L. S., Ledbetter, J. A. & Damle, N. K. Beta 2-integrin LFA-1 signaling through phospholipase C-gamma 1 activation. *Proc. Natl. Acad. Sci. USA* 90, 7099-7103 (1993)) are known to be activated by laminin. To see whether any of these kinases are involved in laminin-dependent membrane translocation of KRS, the present inventors blocked each of these kinases with their specific inhibitors, and checked how these treatments would affect the membrane translocation of KRS. Laminin-dependent increase of KRS and 67LR in the membrane fraction was blocked in the presence of LY294002, the PI3K inhibitor whereas the cells treated with U73122 or staurosporin still showed laminin-dependent induction of 67LRS as the control cells (FIG. 9 upper and data not shown). None of these kinases affected the cytoplasmic level of KRS (FIG. 9 lower). These results imply that PI3K should be involved in laminin-induced phosphorylation of KRS. In fact, phosphorylated KRS at threonine and serine, but not at tyrosine was increased by laminin treatment, but blocked in the presence of LY294002 while staurosporin did not give any effect (FIG. 10). The present inventors then checked whether the laminin-induced phosphorylation of KRS would be necessary for its interaction with 67LR. The treatment of LY294002 suppressed the laminin-induced association of KRS with 67LR (FIG. 11). Since cytoplasmic KRS is anchored to the multi-ARS complex, the present inventors also checked whether laminin-dependent phosphorylation of KRS would affect its association with the multi-ARS complex by co-immunoprecipitation of KRS with glutamyl-prolyl-tRNA synthetase (EPRS), another enzyme component of the complex. In the absence of LY compound, laminin treatment decreased the association of KRS with EPRS with the simultaneous increase of KRS in immuno-depleted soluble fraction (FIG. 12 left lanes in upper and lower panels). In contrast, the KRS binding to EPRS was not affected by laminin treatment when the cells were pre-treated with LY294002 compound (FIG. 12 right lanes in upper and lower panels), suggesting that the phosphorylation of KRS is necessary for the laminin-dependent dissociation of KRS from the complex.

Figure 13:
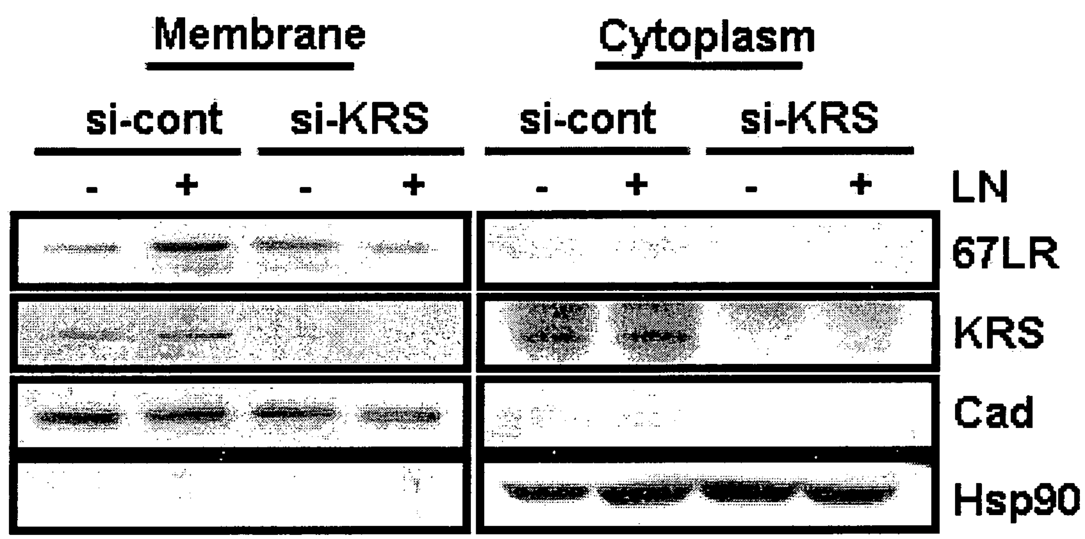
FIG. 13 is the result of Western blotting to confirm 67LR and KRS levels in A549 cell transfected with si-control or si-KRS.
Figure 14:
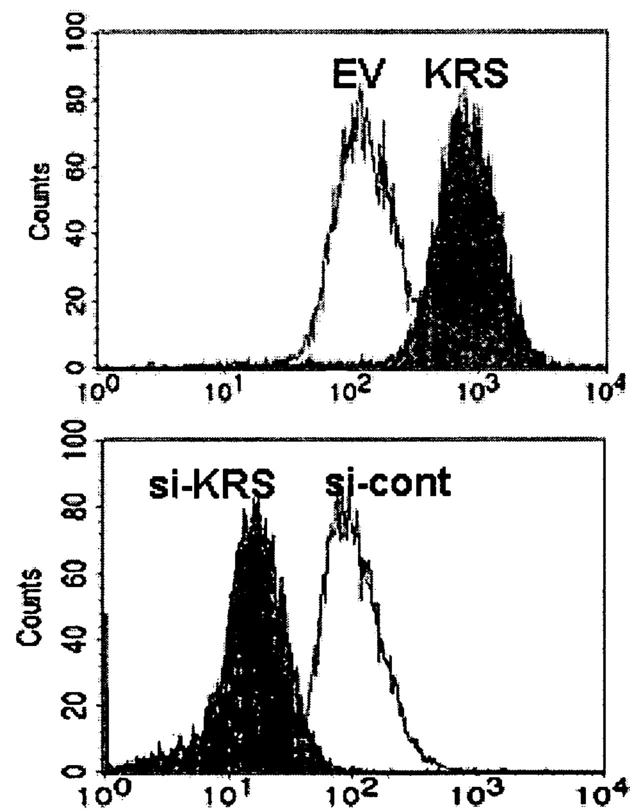
FIG. 14 is the result of flow cytometry to confirm the membrane-bound 67LR level in A549 cells.
Figure 15:
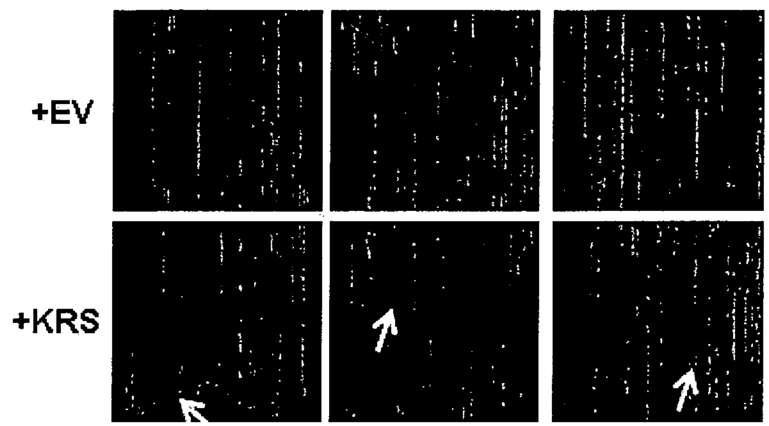
FIG. 15 is the result of immunofluorescence staining to confirm cellular distribution of 67LR in A549 cell with EV (empty vector) or KRS.
Figure 23:
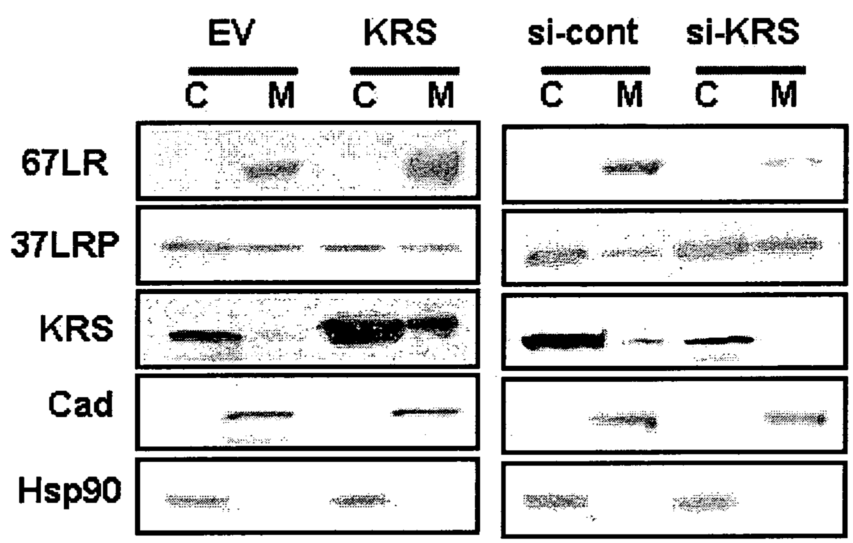
FIG. 23 is the result of Western blotting to confirm membrane level of 67LR depends on KRS expression.

The present inventors then checked whether KRS would affect the membrane level of 67LR in A549 cells. The 67LR level was increased by laminin but the laminin effect was abolished when KRS was suppressed with its specific siRNA (FIG. 13 left), indicating the importance of KRS in laminin-dependent enhancement of 67LR. The present inventors also monitored membrane-bound 67LR by flow cytometry. The membrane 67LR level increased and decreased when the cells were transfected with KRS and si-KRS, respectively (FIG. 14). Cellular distribution of laminin receptor was compared between A549 cells transfected with EV or KRS by immunoflurescence staining. Laminin receptor was more densely stained in plasma membrane regions in KRS-overexpressing cells compared to that in the control cells (FIG. 15). The positive correlation between KRS and 67LR level was further confirmed by measuring 67LR in membrane and cytoplasm according to the variation of KRS level (FIG. 23).

Figure 16:
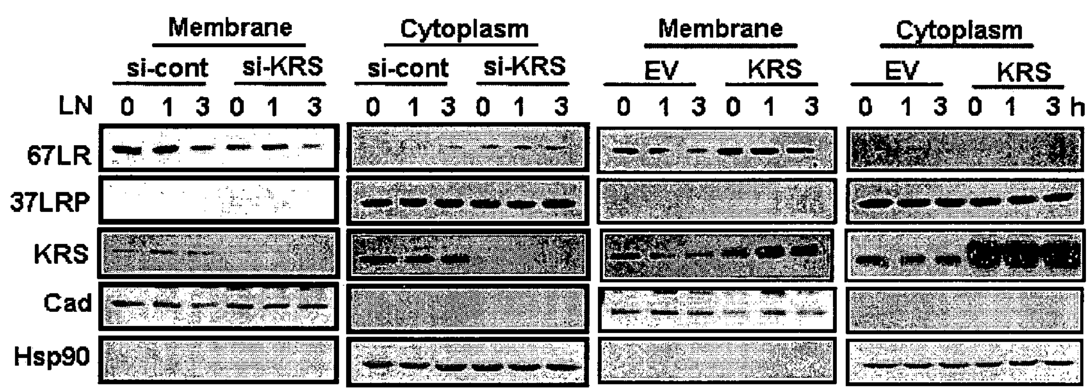
FIG. 16 is the result of Western blotting to confirm the effect of KRS levels on 67LR level in membrane and cytoplasm in A549 cells inhibited de novo protein synthesis.
Figure 17:
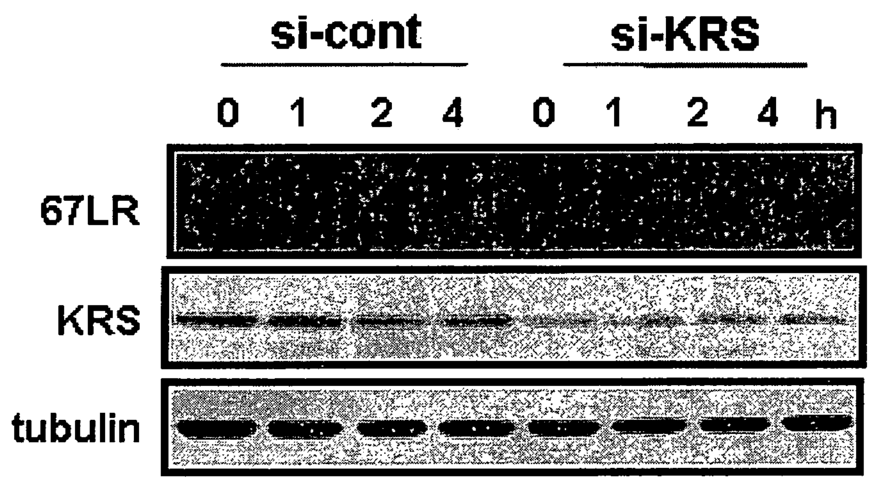
FIG. 17 is the result of pulse-chase experiment confirming the importance of KRS for cellular stability of 67LR.

The present inventors then investigated how KRS enhances membrane level 67LR. KRS can stimulate the 67LR synthesis through transcription or conversion from 37LRP. However, transfection of KRS did not increase. LR transcription (data not shown), excluding its potential role in the regulation of LR transcription. Besides, since KRS showed poor binding to 37LRP in cytoplasm (FIGS. 4 and 5), it is unlikely that it stimulates the conversion process of 37LRP to 67LR. The present inventors also checked whether KRS would mediate fatty acylation of 37LRP since this modification is known to be prerequisite for the conversion of 37LRP to 67LR (Landowski, T. H., Dratz, E., A. & Starkey, J. R. Studies of the structure of the metastasis-associated 67 kDa laminin binding protein: fatty acid acylation and evidence supporting dimerization of the 32 kDa gene product to form the mature protein. *Biochemistry* 34, 11276-11287 (1995); Buto, S. et al. Formation of the 67-kDa laminin receptor by acylation of the precursor. *J. Cell. Biochem.* 69, 244-251 (1998)). In our assay, KRS did not affect the fatty acylation of 37LRP either (data not shown). Since KRS can extend cellular stability of the membrane-bound 67LR, the present inventors checked whether KRS would interfere with endocytosis of membrane-bound 67LR. To see this possibility, the present inventors arrested de novo protein synthesis with cycloheximide and examined whether KRS would affect the 67LR level in membrane and cytoplasm. When KRS expression was suppressed with its specific siRNA, the membrane level of 67LR was decreased with concurrent increase of 67LR in the cytoplasmic fraction (FIG. 16 left). Conversely, overexpression of KRS increased the membrane level of 67LR as above (FIG. 16 right). Based on these results, KRS appears to extend the membrane residency of 67LR by blocking its re-entry to cytoplasm. The present inventors further investigated the effect of KRS on turnover of 67LR by pulse-chase experiment. Nascent protein synthesis was labeled with radioactive methionine and then blocked with cycloheximide. Then, disappearance of 67LR was monitored by autoradiography at time interval. 67LR was rapidly decreased when KRS was suppressed with its siRNA whereas its level was well sustained in si-control cells during this time frame (FIG. 17). Thus, KRS seems to extend half life of 67LR through its association with 67LR in plasma membrane, thereby inhibiting endocytosis of 67LR although degradation process of 67LR needs further investigation.

Figure 18:
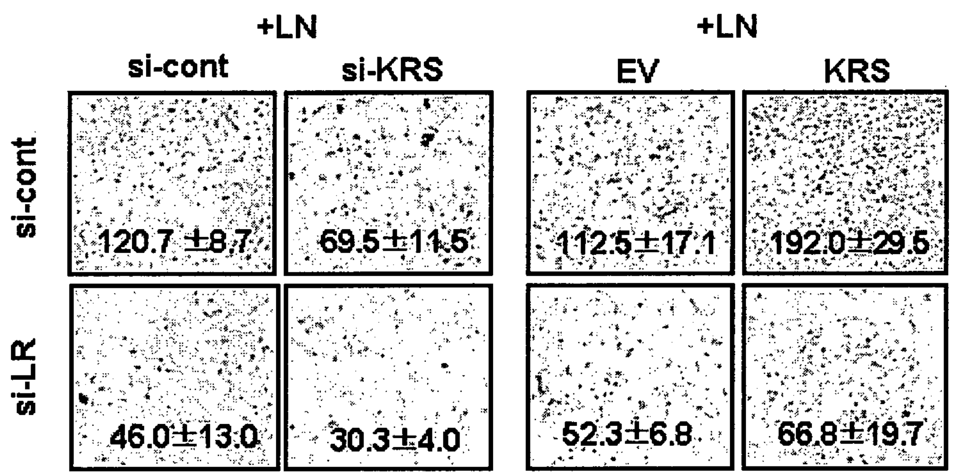
FIG. 18 is the result confirming the effect on cell migration when the expressions of KRS and/or 67LR are inhibited.
Figure 19:
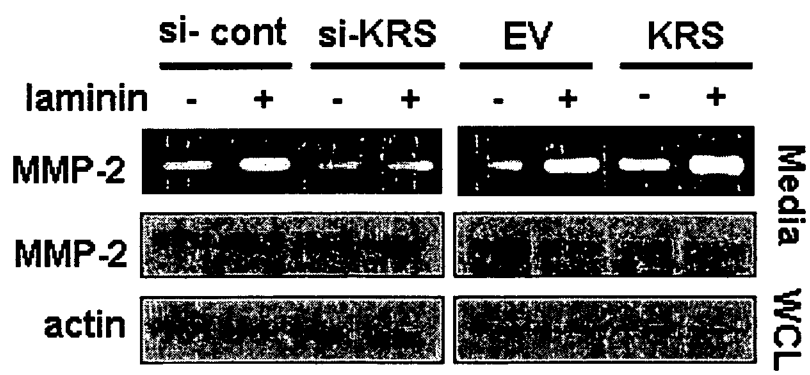
FIG. 19 is the result of zymography and Western blotting to determine MMP-2 activity and level when the expressions of KRS and/or 67LR are inhibited.
Figure 20:
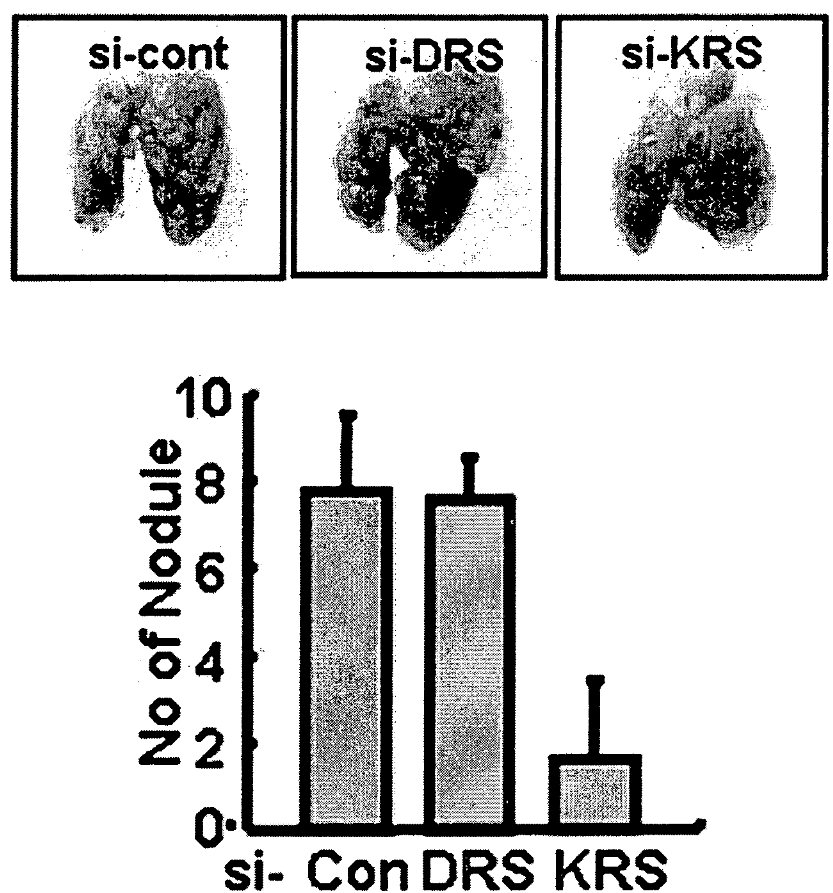
FIG. 20 shows the number of tumor nodules when the expressions of KRS are inhibited in mouse transplanted with 4T-1 cells.
Figure 24:
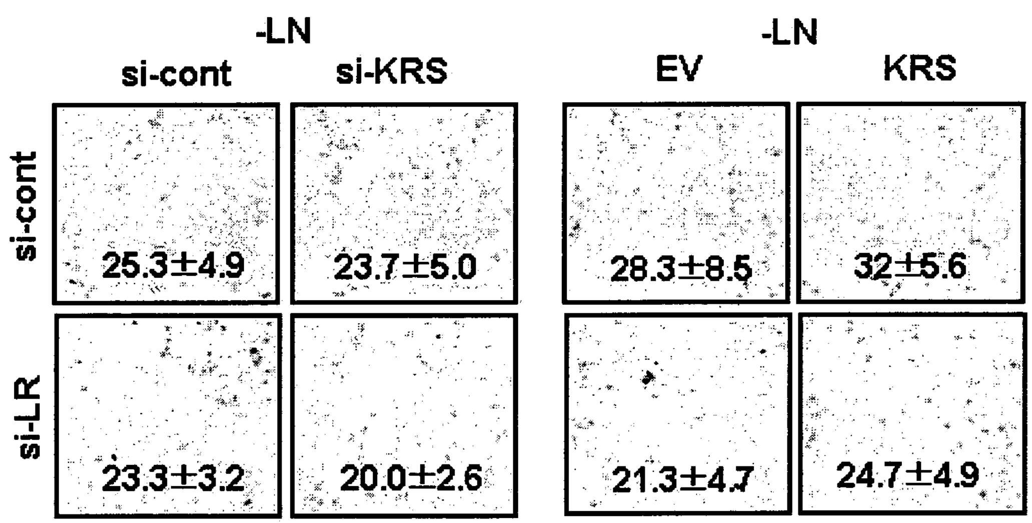
FIG. 24 is the result of measuring migration of A549 cells in the absence of laminin.
Figure 25:
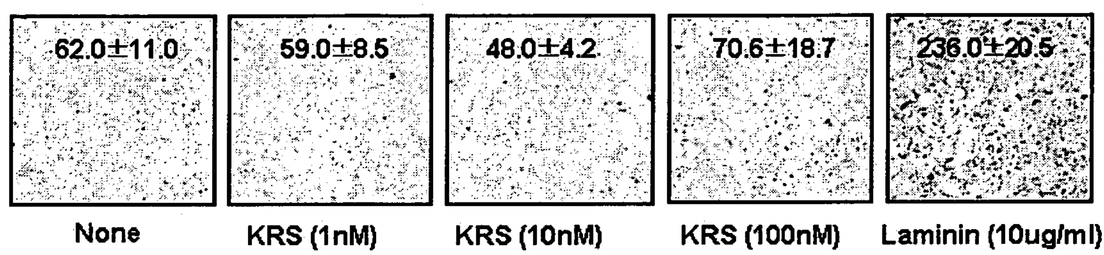
FIG. 25 is the result of measuring the chemotactic activity of KRS in cell migration.
Figure 26:
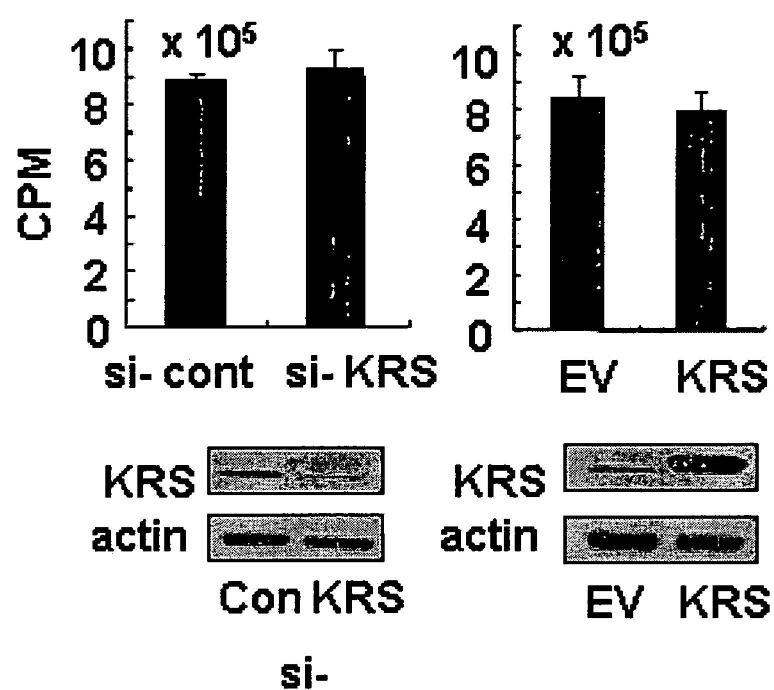
FIG. 26 is the result of confirming KRS level and total protein synthesis in A549 cells by introduction of siRNA and exogenous KRS.
Figure 27:
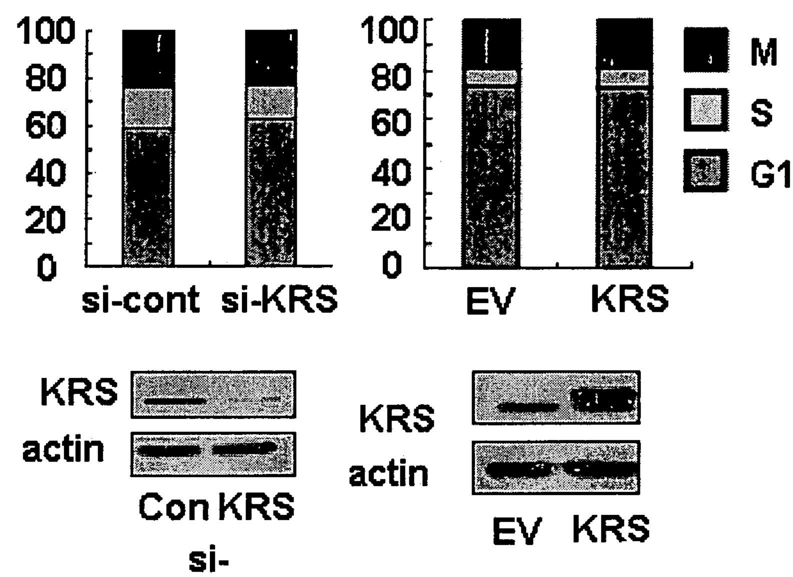
FIG. 27 is the result of confirming KRS level and cell cycle in A549 cells by introduction of siRNA and exogenous KRS.

The present inventors then investigated whether KRS expression level would affect laminin-dependent A549 cell migration using Transwell membrane assay. Migration of the control cells was enhanced about 6 fold in average by laminin treatment (FIG. 24 and FIG. 18). However, the laminin-dependent cell migration was reduced when KRS was suppressed with its specific siRNA (FIG. 18, si-control and si-KRS). Conversely, KRS overexpression further augmented cell migration induced by laminin treatment (FIG. 18, EV and KRS). However, the KRS effect on cell migration was diminished when laminin receptor was suppressed with its siRNA (FIG. 18 si-LR, bottom panel). Since KRS is also secreted in some cancer cells as cytokine (Park, S. G. et al. Human lysyl-tRNA synthetase is secreted to trigger pro-inflammatory response, *Proc. Natl. Acad. Sci. USA* 102, 6356-6361 (2005)), the present inventors checked whether extracellular KRS would affect cell migration. When A549 cells were treated with purified KRS at different concentration, cell migration was little affected (FIG. 25), excluding the extracellular effect of KRS in this assay. Besides, cellular protein synthesis and cell cycle were not influenced by suppression or overexpression of KRS during the period of experiments (FIGS. 26 and 27), indicating that KRS-dependent cell migration did not result from its effect on these processes either. Since laminin treatment results in the activation of MMP-2 (matrix metllo-proteinase-2)(Givant-Horwitz, V., Davidson, B. & Reich, R. Laminin-induced signaling in tumor cells; the role of the M(r) 67,000 laminin receptor. *Cancer Res.* 64, 3572-3579 (2004)), the present inventors checked the effect of KRS on the laminin-dependent activation of MMP-2 using in vitro zymography assay. MMP-2 activity was enhanced by laminin, which was blocked in the presence of si-KRS (FIG. 19 left), but further enhanced by overexpression of KRS (FIG. 19 right). The expression level of MMP-2 was not affected by KRS (FIG. 19 bottom).

Figure 21:
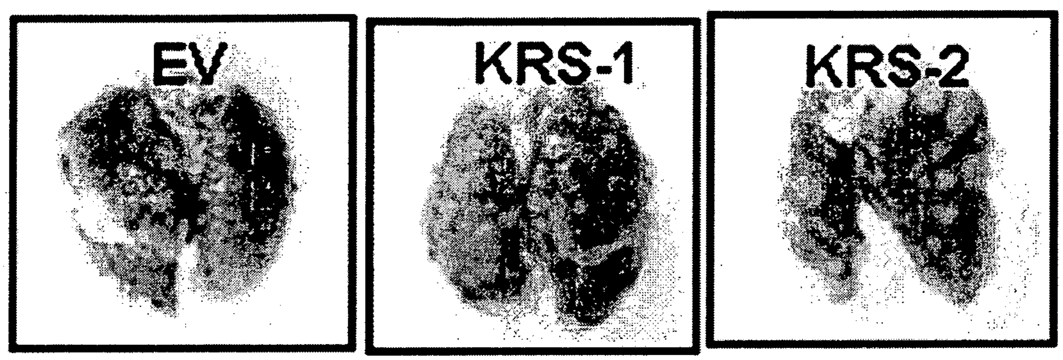
FIG. 21 shows the number tumor nodules when the expressions of KRS are enhanced in mouse transplanted with 4T-1 cells.
Figure 21:
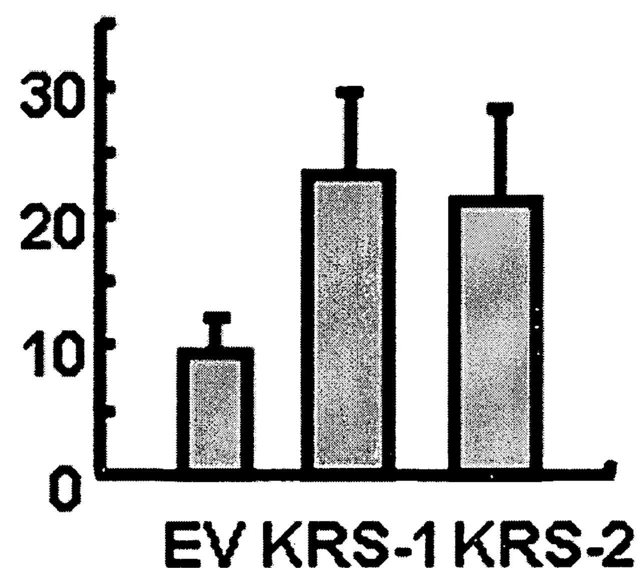
Figure 28:
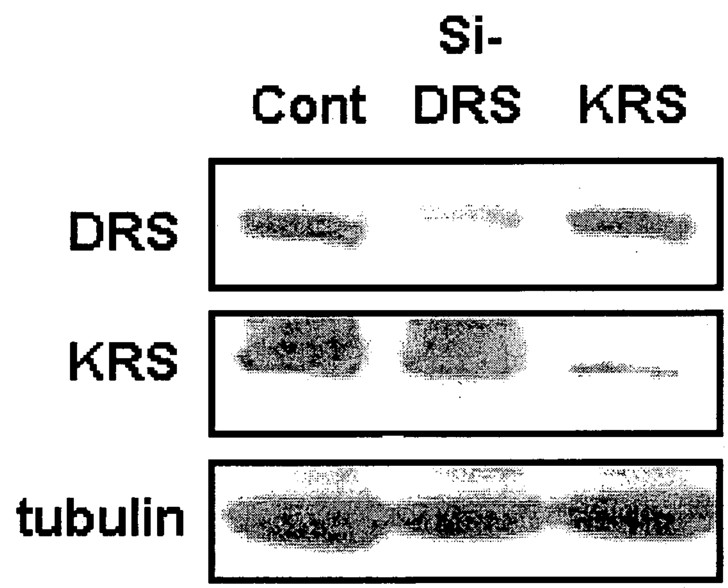
FIG. 28 is the result of Western blotting to confirm the effect of si-KRS and si-DRS on the expression of their target proteins.
Figure 29:
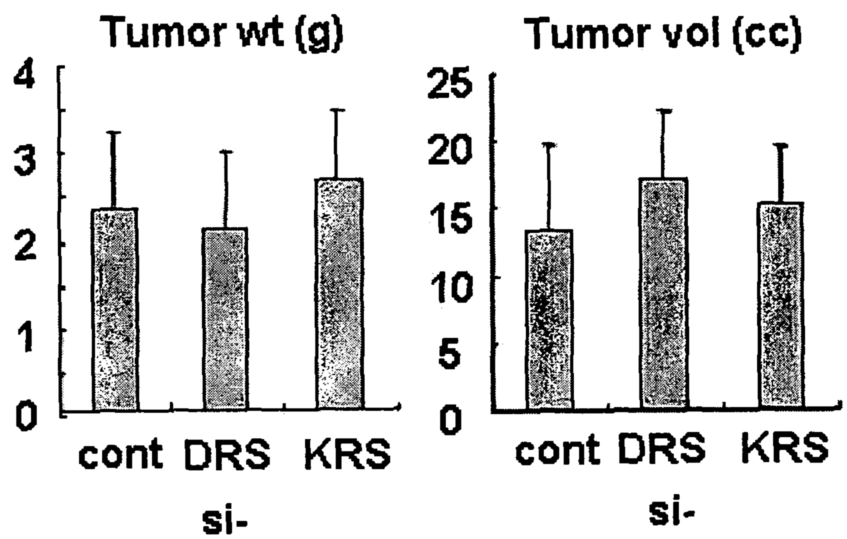
FIG. 29 is the result of confirming the effect of KRS and DRS suppression on primary tumor growth in tumor cell transplantation.
Figure 30:
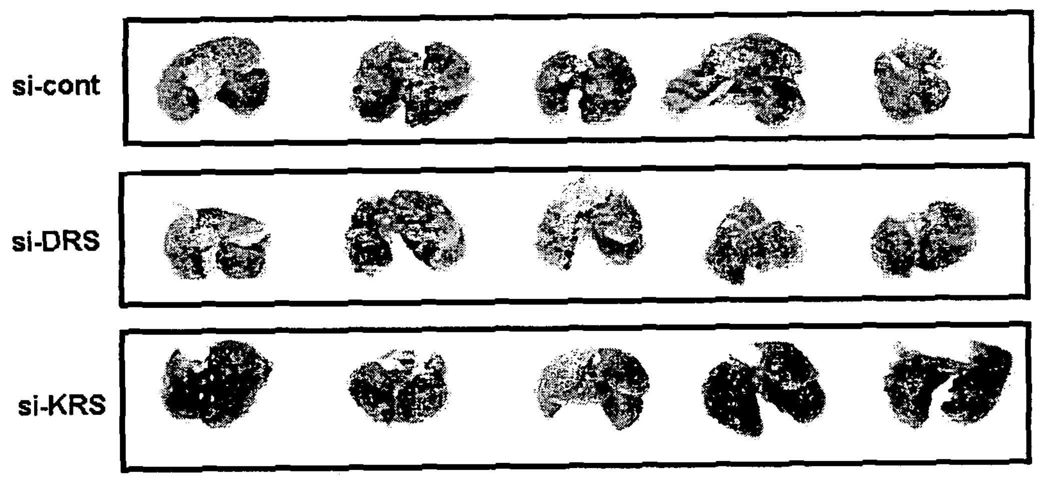
FIG. 30 is the result of confirming the number and size of metastatic tumor nodule in tumor cell transplantation.
Figure 31:
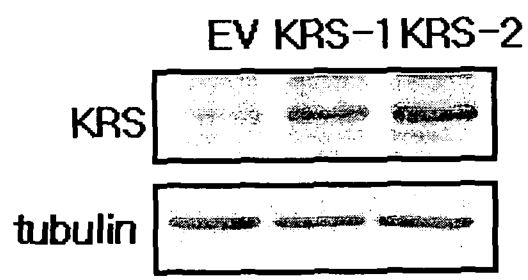
FIG. 31 is the result of Western blotting to confirm overexpression of KRS in KRS-1 and -2 cell lines.
Figure 32:
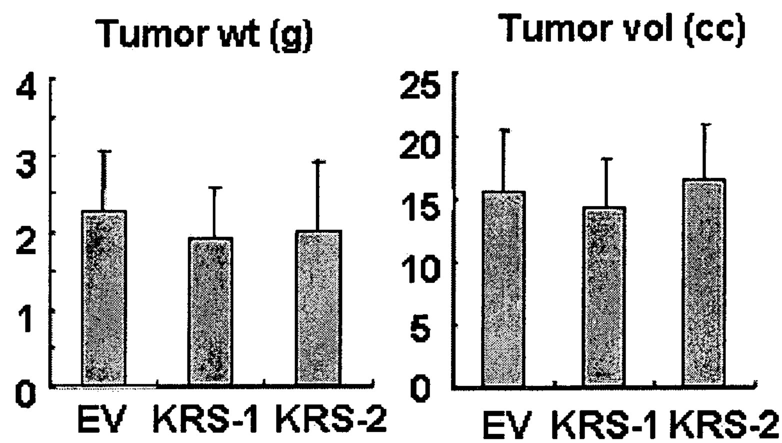
FIG. 32 is the result of confirming the effect of KRS overexpression on primary tumor growth in tumor cell transplantation.
Figure 33:
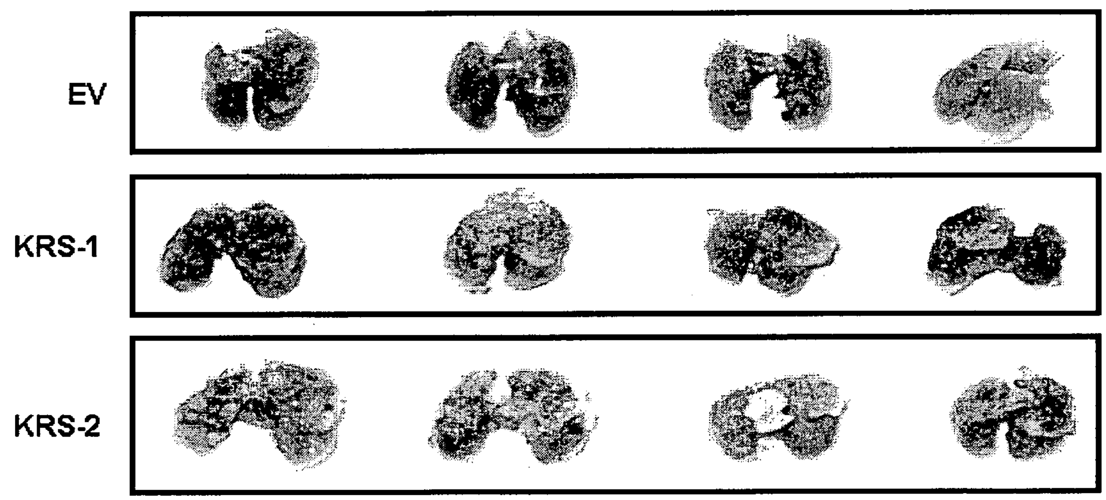
FIG. 33 is the result of confirming the number and size of metastatic tumor nodule in tumor cell transplantation.

Since KRS can induce cell migration via 67LR that is implicated in cancer metastasis, the present inventors examined whether cancer metastasis would be also affected by the expression level of KRS using 4T-1 mouse mammary carcinoma cells that are highly metastatic to lung. The present inventors suppressed either KRS or DRS (aspartyl-tRNA synthetase), another component of multi-ARS complex, with their specific siRNAs and compared how down-regulation of KRS and DRS would affect cancer metastasis. After confirming the suppression effect of si-KRS and -DRS by Western blotting (FIG. 28), each of these cells and the cells with si-control was subcutaneously injected into the back skin of Balb/c mice. All of the three injected cells developed tumors of similar the present inventor sight and volume (FIG. 29), suggesting that KRS level did not affect the growth of primary tumors. Lungs were isolated 21 days after inoculation and the numbers of the metastatic tumor nodules (larger than 1 mm in diameter) were compared between the three groups. The number of the metastatic nodules was significantly decreased by the suppression of KRS compared to those obtained from the control and DRS-suppressed cells (FIG. and FIG. 30). Conversely, the present inventors examined whether overexpression of KRS would enhance cancer metastasis using the same method as above. The present inventors first established 4T-1 cell lines stably overexpressing KRS by transfection of the KRS-encoding plasmid and G418 screening. KRS overexpression in the established cell lines were confirmed by Western blotting, and the present inventors selected the two different cells (KRS-1 and KRS-2) expressing KRS at higher amount than those transfected with empty vector (FIG. 31). These cells also generated primary tumors of similar weight and size (FIG. 32). When the present inventors examined the lungs in 30 days after inoculation of the cells, both of the KRS-overexpressing cells generated more nodules compared to the control cells (FIG. 21 and FIG. 33). All of these results suggest that KRS can induce cancer metastasis in vivo.

Since cancer-specific overexpression of laminin receptor has been frequently observed (Fontanini, G. et al. 67-Kilodalton laminin receptor expression correlates with worse prognostic indicators in non-small cell lung carcinomas. *Clin. Cancer Res.* 3, 227-231 (1997), Viacava, P. et al. The spectrum of 67-kD laminin receptor expression in breast carcinoma progression. *J. Pathol.* 182, 36-44 (1997), the present inventors analyzed whether overexpression of 67LR is also associated with that of KRS by immunohistochemical staining of 67LR and KRS in lung and breast cancers as the examples. Among the 39 examined lung cancer tissues, 67LR overexpression was observed in 21 cases (54%), in which KRS level was also increased in 19 cases (about 90%) (Table 1 and FIG. 22 upper). Likewise, the 21 cases out of the 40 examined breast cancer patients showed 67LR overexpression. In these cases, all 21 cases also showed increased level of KRS (Table 1 and FIG. 22 lower). In both cases, the tight linkage between the expressions of the two proteins is shown although it is to be determined whether their coexpression in cancer is actually implicated in metastasis.

TABLE 1

| | 67LR Normal | 67LR Overexpression | Total |
|---|---|---|---|
| lung cancer | | | |
| KRS Normal | 10 | 2 | 12 |
| KRS Overexpression | 8 | 19 | 27 |
| Total | 18 | 21 | 39 |
| * fisher's exact test p = 0.001 | | | |
| Breast cancer | | | |
| KRS Normal | 5 | 0 | 5 |
| KRS Overexpression | 14 | 21 | 35 |
| Total | 19 | 11 | 40 |

* fisher's exact test p = 0.018

At this time, it may be referred as followed regarding the table 1. The table 1 is the correlation between 67LR and KRS expression in cancer tissues. To test whether expression level of 67LR is associated with that of KRS, tissue microarrays of lung and breast cancer patients were subjected to immunohistochemical staining with their respective antibodies, and the relative expression levels of the two proteins were determined. MLuC5 antibody was used for immunodetection of 67LR. Expression level was determined by staining intensity of the specimen and classified into 4 groups (score 0, 1, 2, and 3). In the final evaluation, the samples were divided into normal (with a score 0 or 1) and overexpression group (with a score 2 or 3). Statistical analyses were performed using the Pearson $X^2$ test and Student t test to evaluate the correlation between 67LR and KRS expression. P values<0.05 were considered significant. All statistical analyses were performed using SPSS v11.5 software (SPSS, Chicago, Ill.).

Figure 22:
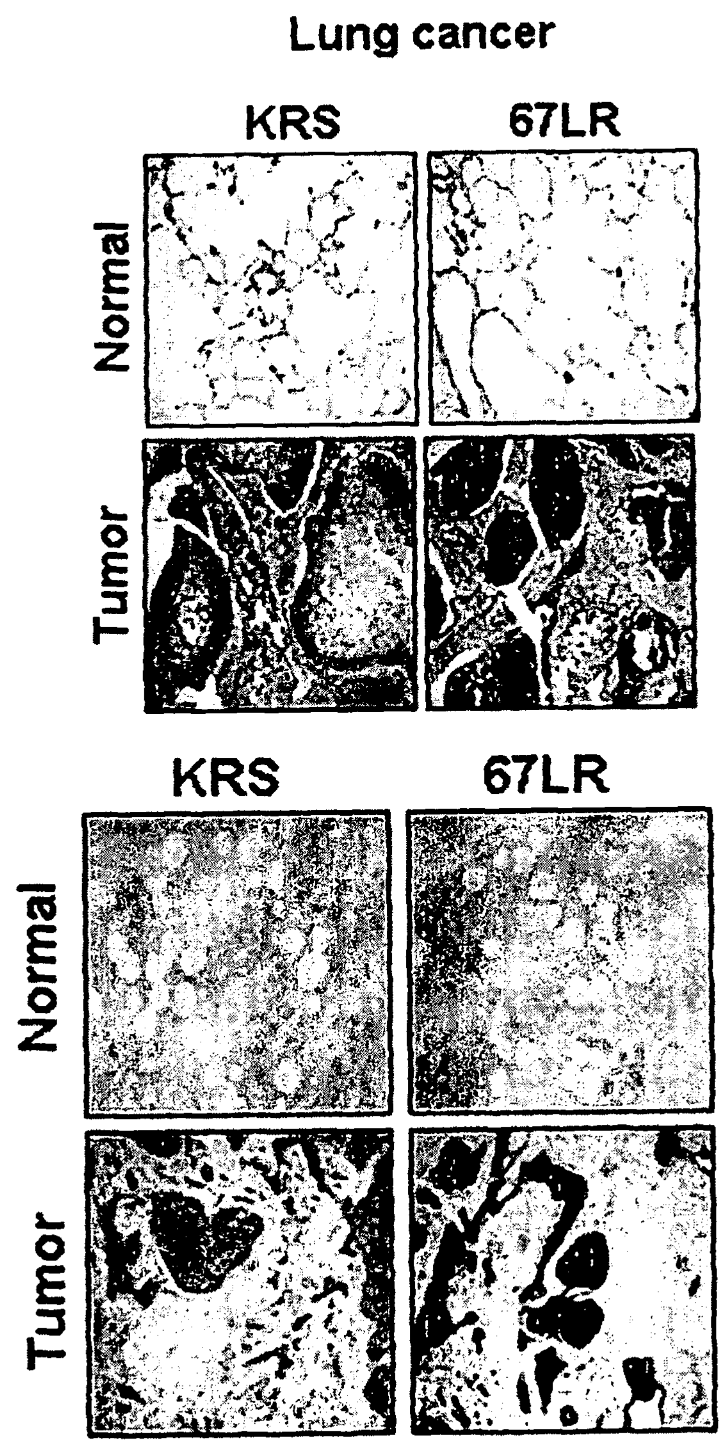
FIG. 22 is the result of immunohistochemical staining to confirm the expression levels of KRS and 67LR in lung and breast cancer tissues.

Many translational factors including ribosomal components are pleiotropic (Wool, I. G. Extraribosomal functions of ribosomal proteins *Trends Biochem. Sci.* 21, 164-165 (1996)) and associated with various tumorigenesis (Lee, S. W., Kang, Y. S. & Kim, S. Multi-functional proteins in tumorigenesis: Aminoacyl-tRNA synthetases and translational components. *Curr. Proteomics* 3, 233-247 (2006)). Here the present inventors demonstrated that two translational factors, KRS and p40/37LRP, work together for cell migration and cancer metastasis in vivo (FIGS. 18 and 22). At this moment, the present inventors do not know whether the potential association of these two proteins is the evolutionary coincidence or has another physiological reason in protein synthesis that needs to be understood in the future. Among the components of the multi-ARS complex, KRS is the most stable protein and required for the stability of other components (Han, J. M. et al. Hierarchical Network between the components of the multi-tRNA synthetase complex: Implications for complex formation. *J. Biol. Chem.* 281, 38663-38667 (2006)), implying its potential to stabilize the associated proteins. Here the present inventors showed that KRS also extends cellular stability of 67LR (FIG. 17).

The association of KRS with 67LR may have different functional implications. Under physiological condition, a portion of cytoplasmic KRS is phosphorylated and mobilized to the plasma membrane by various growth-stimulatory or survival signals to bind 67LR that mediates laminin signal. In cancer cells, membrane level of KRS could be abnormally enhanced either due to its overexpression or its constitutive membrane translocation resulting from the hyperactivated upstream kinases such as PI3K. Perhaps, these excess KRS could be driven to the plasma membrane that is either recruited to 67LR or secreted. In addition, it is worth noting that the deregulated activation of PI3K is often associated with tumor growth and metastasis (Wymann, M. P. & Marone, R. Phosphoinositide 3-kinase in disease: timing, location, and scaffolding. *Curr. Opin. Cell Biol.* 17, 141-149 (2005)), and laminin promotes cancer invasion via PI3K (Baba, Y. et al. Laminin-332 promotes the invasion of oesophageal squamous cell carcinoma via PI3K activation. *Br. J. Cancer* 98, 974-980 (2008)). The constitutive activation of PI3K may lead to the phosphorylation of KRS that would be mobilized to the membrane. Either or both of these conditions could contribute to the increase of 67LR in the plasma membrane, thereby amplifying the laminin signaling for cancer metastasis. Much investigation is being made to control metastatic spread of cancer. In this regard, KRS activity in cancer metastasis via 67LR may provide a previously unexplored window for cancer diagnosis and therapy.

INDUSTRIAL APPLICABILITY

As can be seen from the foregoing, the present inventors disclosed that the inventive KRS interacts with 67LR through translocation of KRS into plasma membrane, and so enhances tumor (or cancer) cell migration, thereby having an effect on cancer metastasis. In addition, we also disclosed that KRS overexpression or inhibition of KRS expression can modulate tumor (or cancer) cell metastasis through in vivo experiments using mice. Accordingly, cancer metastasis and cancer cell migration may be controlled using the inventive KRS, further the cellular metabolism related to laminin receptor (67LR) of plasma membrane may be controlled. The relationship between KRS and laminin receptor disclosed in the present invention may be very useful for treatment, prevention and/or diagnosis of various disease related to thereof.

The invention claimed is:

1. A method for inhibiting cancer metastasis, comprising:

(a) reducing an intracellular level of lysyl tRNA synthetase (KRS); and (b) inhibiting an interaction between intracellular lysyl tRNA synthetase (KRS) and laminin receptor (67LR) with an agent that inhibits intracellular KRS activity or an agent that inhibits an interaction between intracellular KRS and 67LR, wherein the inhibited interaction between intracellular KRS and 67LR inhibits cancer metastasis, wherein the agent is selected from the group consisting of an antisense RNA against a polynucleotide encoding KRS, a siRNA against a polynucleotide encoding KRS, and an antibody against KRS.

2. The method of claim 1, wherein the lysyl tRNA synthetase (KRS) consists of the amino acid sequence represented by SEQ ID NO: 1.

3. A method for inhibiting cancer cell migration, comprising:

(a) reducing an intracellular level of lysyl tRNA synthetase (KRS); and (b) inhibiting an interaction between intracellular lysyl tRNA synthetase (KRS) and laminin receptor (67LR) with an agent that inhibits intracellular KRS activity or an agent that inhibits an interaction between intracellular KRS and 67LR, wherein the inhibited interaction between intracellular KRS and 67LR inhibits cancer cell migration, wherein the agent is selected from the group consisting of an antisense RNA against a polynucleotide encoding KRS, a siRNA against a polynucleotide encoding KRS, and an antibody against KRS.

4. The method of claim 1, wherein the lysyl tRNA synthetase (KRS) consists of the amino acid sequence represented by SEQ ID NO: 1.

* * * * *